US012629053B2

(12) United States Patent
Kostic et al.

(10) Patent No.: US 12,629,053 B2
(45) Date of Patent: May 19, 2026

(54) EXIT DETECTION SYSTEM WITH COMPENSATION

(71) Applicant: Stryker Corporation, Portage, MI (US)

(72) Inventors: Marko N. Kostic, Oshawa (CA); Jonathan Mark Greenbank, Plainwell, MI (US)

(73) Assignee: Stryker Corporation, Portage, MI (US)

( * ) Notice: Subject to any disclaimer, the term of this patent is extended or adjusted under 35 U.S.C. 154(b) by 50 days.

(21) Appl. No.: 18/918,181

(22) Filed: Oct. 17, 2024

(65) Prior Publication Data

US 2025/0031999 A1 Jan. 30, 2025

Related U.S. Application Data

(60) Division of application No. 16/823,923, filed on Mar. 19, 2020, now Pat. No. 12,144,607, which is a (Continued)

(51) Int. Cl.
*A61B 5/11* (2006.01)
*A61B 5/00* (2006.01)
(Continued)

(52) U.S. Cl.
CPC .......... *A61B 5/1115* (2013.01); *A61B 5/6891* (2013.01); *A61G 7/005* (2013.01); *A61G 7/012* (2013.01); *A61G 7/015* (2013.01); *A61G 7/018* (2013.01); *A61G 7/0524* (2016.11); *A61G 13/04* (2013.01); *A61G 13/06* (2013.01);
(Continued)

(58) Field of Classification Search
CPC ........ A61G 7/002; A61G 7/005; A61G 7/012; A61G 7/015; A61G 7/018; A61G 7/05; A61G 7/0507; A61G 7/0524; A61G 7/0527; A61G 13/02; A61G 13/04; A61G 13/06; A61G 13/08; A61G 2203/32; A61G 2203/42; A61B 5/1115; A61B 5/1113; A61B 5/11; A61B 5/6891
USPC .............. 5/613, 616–618, 611, 600, 11, 425, 5/428–430
See application file for complete search history.

(56) References Cited

U.S. PATENT DOCUMENTS

| | | | |
|---|---|---|---|
| 7,690,059 B2 * | 4/2010 | Lemire | A61G 7/005 5/616 |
| 7,805,784 B2 * | 10/2010 | Lemire | A61G 7/0506 108/147 |

(Continued)

*Primary Examiner* — Robert G Santos
(74) *Attorney, Agent, or Firm* — Gardner, Linn, Burkhart & Ondersma LLP

(57) ABSTRACT

A person support apparatus, such as a bed, stretcher, cot, recliner, or the like, includes an exit detection system having a plurality of force sensors that support the weight of an occupant positioned on a support surface. The force sensors are part of an exit detection system that issues an alarm when the occupant exits, or is about to exit, the person support apparatus. The distribution of weight applied to the force sensors is used to determine if the occupant is about to exit the person support apparatus. Compensation is made to the exit detection system for changes in the weight distribution that are not caused by movement of the occupant. Such changes may be due to siderail movement, support surface pivoting, and/or movement of other components of the person support apparatus.

13 Claims, 9 Drawing Sheets

Related U.S. Application Data continuation of application No. 14/918,003, filed on Oct. 20, 2015, now Pat. No. 10,617,327.

(60) Provisional application No. 62/076,005, filed on Nov. 6, 2014.

(51) Int. Cl.

| | |
|---|---|
| *A61G 7/005* | (2006.01) |
| *A61G 7/012* | (2006.01) |
| *A61G 7/015* | (2006.01) |
| *A61G 7/018* | (2006.01) |
| *A61G 7/05* | (2006.01) |
| *A61G 13/04* | (2006.01) |
| *A61G 13/06* | (2006.01) |
| *A61G 13/08* | (2006.01) |

(52) U.S. Cl.

CPC ............ *A61G 13/08* (2013.01); *A61B 5/1113* (2013.01); *A61G 7/0507* (2013.01); *A61G 2203/32* (2013.01); *A61G 2203/42* (2013.01)

(56) References Cited

U.S. PATENT DOCUMENTS

| | | | | |
|---|---|---|---|---|
| 7,861,334 | B2 * | 1/2011 | Lemire | A61G 7/0507 5/280 |
| 7,962,981 | B2 * | 6/2011 | Lemire | B60T 17/22 5/616 |
| 8,701,229 | B2 * | 4/2014 | Lemire | A61G 7/005 5/510 |
| 9,038,217 | B2 * | 5/2015 | Elliot | G16Z 99/00 5/617 |
| 9,555,778 | B2 * | 1/2017 | Lemire | B60T 17/22 |
| 9,815,439 | B2 * | 11/2017 | Lemire | A61G 7/012 |
| 10,130,536 | B2 * | 11/2018 | Roussy | A61G 7/0512 |
| 10,188,569 | B2 * | 1/2019 | Elku | A61G 7/002 |
| 10,357,185 | B2 * | 7/2019 | Kostic | A61B 5/1036 |
| 10,507,158 | B2 * | 12/2019 | Brzenchek | A61G 7/0506 |
| 10,617,327 | B2 * | 4/2020 | Kostic | A61G 7/005 |
| 10,716,722 | B2 * | 7/2020 | Roussy | A61G 7/0512 |
| 10,786,408 | B2 * | 9/2020 | Sidhu | A61G 13/06 |
| 10,842,694 | B2 * | 11/2020 | Roussy | A61G 7/0528 |
| 10,952,920 | B2 * | 3/2021 | Brzenchek | A61H 1/008 |
| 11,058,325 | B2 * | 7/2021 | Kostic | A61G 7/0524 |
| 11,285,061 | B2 * | 3/2022 | Roussy | A61G 7/0512 |
| 11,419,776 | B2 * | 8/2022 | Roussy | A61G 7/0507 |
| 11,490,834 | B2 * | 11/2022 | Sukumaran | G08B 21/0461 |
| 11,699,517 | B2 * | 7/2023 | Receveur | H04B 17/318 705/2 |
| 11,730,400 | B2 * | 8/2023 | Kostic | A61B 5/6891 340/573.1 |
| 11,800,995 | B2 * | 10/2023 | Sukumaran | G08B 29/185 |
| 11,865,056 | B2 * | 1/2024 | Roussy | A61G 7/018 |
| 11,980,580 | B2 * | 5/2024 | Roussy | A61G 7/0509 |
| 12,144,607 | B2 * | 11/2024 | Kostic | A61G 7/018 |
| 12,268,642 | B2 * | 4/2025 | Sidhu | A61B 5/1115 |
| 12,408,845 | B2 * | 9/2025 | Sukumaran | A61G 7/0507 |
| 2007/0157385 | A1 * | 7/2007 | Lemire | A61G 7/0524 5/618 |
| 2007/0163043 | A1 * | 7/2007 | Lemire | A61G 7/0516 5/618 |
| 2007/0169268 | A1 * | 7/2007 | Lemire | A61G 7/015 5/617 |
| 2007/0174964 | A1 * | 8/2007 | Lemire | A61G 7/0528 5/430 |
| 2008/0172789 | A1 * | 7/2008 | Elliot | A61G 7/0527 5/616 |
| 2011/0162141 | A1 * | 7/2011 | Lemire | A61G 7/015 188/1.12 |
| 2014/0237721 | A1 * | 8/2014 | Lemire | A61G 7/1046 188/1.12 |
| 2016/0106345 | A1 * | 4/2016 | Kostic | A61B 5/6892 5/652 |
| 2016/0128610 | A1 * | 5/2016 | Kostic | A61G 13/04 5/613 |
| 2016/0193095 | A1 * | 7/2016 | Roussy | A61G 7/0506 5/616 |
| 2016/0287459 | A1 * | 10/2016 | Lemire | A61M 5/1415 |
| 2017/0098359 | A1 * | 4/2017 | Sidhu | A61G 7/012 |
| 2017/0143566 | A1 * | 5/2017 | Elku | A61G 7/0512 |
| 2017/0239131 | A1 * | 8/2017 | Brzenchek | A47C 21/048 |
| 2017/0243459 | A9 * | 8/2017 | Sidhu | A61B 5/1115 |
| 2019/0151170 | A1 * | 5/2019 | Roussy | A61G 7/0516 |
| 2019/0183700 | A1 * | 6/2019 | Roussy | A61G 7/002 |
| 2019/0298229 | A1 * | 10/2019 | Kostic | A61G 7/0524 |
| 2020/0060925 | A1 * | 2/2020 | Brzenchek | A61H 9/0078 |
| 2020/0214599 | A1 * | 7/2020 | Kostic | A61G 7/0524 |
| 2020/0330300 | A1 * | 10/2020 | Roussy | A61G 7/0509 |
| 2021/0007919 | A1 * | 1/2021 | Sidhu | A61G 13/04 |
| 2021/0052197 | A1 * | 2/2021 | Sukumaran | A61G 7/0527 |
| 2021/0065885 | A1 * | 3/2021 | Receveur | G16H 40/67 |
| 2021/0069041 | A1 * | 3/2021 | Roussy | A61G 7/0518 |
| 2021/0315487 | A1 * | 10/2021 | Kostic | A61G 7/0524 |
| 2021/0353179 | A1 * | 11/2021 | Sukumaran | A61G 7/0514 |
| 2022/0218543 | A1 * | 7/2022 | Roussy | A61G 7/018 |
| 2022/0395412 | A1 * | 12/2022 | Roussy | A61G 7/0518 |
| 2023/0067526 | A1 * | 3/2023 | Sukumaran | A61B 5/6891 |
| 2023/0233102 | A1 * | 7/2023 | Paul | A61G 7/001 5/611 |
| 2023/0298740 | A1 * | 9/2023 | Receveur | G16H 40/67 705/2 |
| 2024/0180764 | A1 * | 6/2024 | Roussy | A61G 7/012 |
| 2024/0350339 | A1 * | 10/2024 | Roussy | A61G 7/012 |
| 2025/0031999 | A1 * | 1/2025 | Kostic | A61B 5/1115 |

* cited by examiner

EXIT DETECTION SYSTEM WITH COMPENSATION

CROSS-REFERENCE TO RELATED APPLICATIONS

This application is a divisional of U.S. patent application Ser. No. 16/823,923 filed Mar. 19, 2020, by inventors Marko Kostic et al. and entitled EXIT DETECTION SYSTEM WITH COMPENSATION, which in turn is a continuation of U.S. patent application Ser. No. 14/918,003, filed Oct. 20, 2015, by inventors Marko Kostic et al. and entitled EXIT DETECTION SYSTEM WITH COMPENSATION, which in turn claims priority to U.S. provisional patent application Ser. No. 62/076,005 filed Nov. 6, 2014, by inventors Marko Kostic et al. and entitled EXIT DETECTION SYSTEM WITH COMPENSATION, the complete disclosures of all of which are incorporated herein by reference.

BACKGROUND

The present disclosure relates to person support apparatuses, such as beds, cots, stretchers, operating tables, recliners, or the like. More specifically, the present disclosure relates to person support apparatuses that include sensors for detecting when an occupant of the person support apparatus has exited therefrom, or may be about to exit therefrom.

Existing hospital beds and/or stretchers often include a bed exit system that is adapted to detect when a patient has exited the bed, or when a patient may be about to exit the bed. Typically, such beds include circuitry for providing an audio or visual alert when such an exit or pre-exit situation is detected. In many cases, the bed or stretchers include circuitry for transmitting a signal to a remote location, such as a nurses' station, so that the appropriate caregivers are notified of the exit, or pre-exit condition, and can respond appropriately. Existing exit detection systems often rely on an analysis of the outputs of multiple load cells. In some existing systems, the load cells outputs are monitored to compute a location of the occupant and if that location moves out of a defined area, an exit alert is issued. In other existing systems, the load cell outputs are monitored and one or more ratios of the forces detected by one or more of the load cells are computed. If the one or more ratios change by an amount greater than a threshold amount, an exit alert is issued.

SUMMARY

According to various embodiments, the present disclosure provides an improved person support apparatus having an exit detection system that distinguishes between changes in the exit detection system's sensors that are due to an occupant's movement relative to the support surface of the person support apparatus, and changes in the exit detection system's sensors that are due to factors other than such movement. Such factors include, but are not limited to: (1) pivoting of one or more individual sections of a support deck that is adapted to support the person; (2) tilting a frame that supports the support deck; (3) changing a height of the support deck; (4) changing a position of the support deck relative to a frame; (5) turning the person on the support deck by way of a mattress having inflatable side bladders, or by using another type of turning device; and (6) changing a position of one or more siderails that are attached to the person support apparatus. The exit detection system ignores changes in its sensors that are due to one or more of these factors when determining whether to issue an alert. Alarms issued by the exit detection system are thereby more tightly related to movement of the occupant relative to the support surface, rather than movement of one or more components of the person support apparatus, or movement of the occupant that is due to the movement of the person support apparatus, rather than movement independently undertaken by the occupant.

In at least one embodiment, an exit detection system is provided that does not need to be reset when a component of the person support apparatus (e.g. a siderail, a deck section, a litter frame, etc.) changes. Instead, the effect of those changes is automatically compensated by the exit detection system so that those changes do not contribute to the issuance of an exit alert. The labor of re-setting the exit detection system after changes in the configuration of the person support apparatus is therefore eliminated while avoiding any significant increase in the likelihood of a false exit alert being issued.

According to one aspect of the disclosure, a person support apparatus is provided that includes a support surface, a plurality of force sensors, an angle sensor, and a controller. The support surface supports thereon an occupant of the person support apparatus and it includes a first section and a second section. The first section pivots with respect to the second section about a generally horizontal pivot axis. The plurality of force sensors detect a load that includes the weight of the support deck and, if present, the weight of the occupant. Other components and/or items may also be included in the load. The angle sensor determines an angle of the first section with respect to a reference. The controller issues an alert if outputs from the force sensors meet at least one criterion. The controller takes into account the angle when determining whether to issue the alert or not.

According to another aspect, a person support apparatus is provided that includes a support surface, a plurality of force sensors, a siderail, a siderail sensor, and a controller. The support surface supports thereon an occupant of the person support apparatus. The force sensors detect a load that includes the weight of the support deck and, if present, the weight of the occupant. Other components and/or items may also be included in the load. The siderail is movable between an up position and a down position. The siderail sensor detects whether the siderail is in the up position or the down position. The controller issues an alert if outputs from the force sensors meet at least one criterion. The controller takes into account the current position of the siderail when determining whether to issue the alert or not.

According to another aspect of the disclosure, a person support apparatus is provided that includes a support surface, a plurality of force sensors, a litter frame, a position sensor, and a controller. The support surface supports thereon an occupant of the person support apparatus. The force sensors detect a load that includes the weight of the support deck and, if present, the weight of the occupant. Other components and/or items may also be included in the load. The litter frame supports the support surface and is adapted to move forward toward a head end of the litter frame and move rearward toward a foot end of the litter frame. The position sensor senses a position of the support surface relative to the litter frame. The controller issues an alert if outputs from the force sensors meet at least one criterion. The controller takes into account the current position of the support surface relative to the litter frame when determining whether to issue the alert or not.

According to still another aspect of the disclosure, a person support apparatus is provided that includes a support surface, a plurality of force sensors, a first lift, a second lift, a height sensor, and a controller. The support surface supports thereon an occupant of the person support apparatus. The force sensors detect a load that includes the weight of the support deck and, if present, the weight of the occupant. Other components and/or items may also be included in the load. The first lift changes a height of a first end of the support surface, and the second lift changes a height of a second end of the support surface. The height sensor determines a height of the support surface. The controller issues an alert if outputs from the force sensors meet at least one criterion. The controller takes into account the height of the support surface when determining whether to issue the alert or not.

According to still another aspect of the disclosure, a person support apparatus is provided that includes a support surface, a plurality of force sensors, a litter frame, a litter frame angle sensor, and a controller. The support surface supports thereon an occupant of the person support apparatus. The force sensors detect a load that includes the weight of the support deck and, if present, the weight of the occupant. Other components and/or items may also be included in the load. The litter frame supports the support surface and is adapted to tilt. The litter frame angle sensor determines an angle tilt of the litter frame with respect to horizontal. The controller determines a center of gravity of the load based on outputs from the force sensors and issues an alert if the center of gravity moves outside of a defined area. The controller also estimates an amount by which the center of gravity of the load shifts that is due to changes in the litter frame angle and that is not due to changes in a position of the occupant relative to the support surface.

According to other embodiments, the criterion is a center of gravity of the load moving outside of a defined area. In still other embodiments, the criterion is a change in the output of at least one of the plurality of force sensors exceeding a threshold.

In other embodiments, the controller detects a change in the center of gravity of the load and estimates what portion of the change is due to movement of the occupant relative to the support deck and what portion of the change is due one or more other factors. The one or more other factors include: a change in the angle of the first section of the deck; a change in the position of one or more siderails; a change in the position of the support deck on the litter frame; a change in the height of the support deck; a change in the tilting of the litter frame; and a change in turning angle of a powered mattress supported on the support deck.

In another embodiment, the first section of the support surface is a head section adapted to support a head of the occupant and the second section is a seat section adapted to support the occupant's buttocks.

In another embodiment, the controller takes into account, when determining the center of gravity of the load, a weight of the occupant. The controller also or alternatively takes into account one or more of the following factors: empirical data indicating a relationship between heights of the support deck and changes in the center of gravity of the load; empirical data indicating a relationship between positions of the support deck on the litter frame and changes in the center of gravity of the load; empirical data indication a relationship between an angle of the head section of the support deck and changes in the center of gravity of the load; empirical data indicating a relationship between a position of one or more siderails and changes in the center of gravity of the load; empirical data indicating a relationship between a tilt angle of a frame on which the support deck is supported and changes in the center of gravity of the load; and empirical data indicating a relationship between a turn angle of a powered mattress and changes in the center of gravity of the load.

In still other embodiments, one or more these factors is substituted with weight distribution data derived from calculations using the weight and position of one or more components of the person support apparatus whose weight is detected by the force sensors.

In some embodiments, when the controller estimates what portion of the change in the center of gravity of the load is due to the tilting of the litter frame, the controller utilizes at least one of the following parameters: a type of mattress supported on the support deck, an inflation pressure of the mattress, and a penetration depth of the occupant into the mattress.

According to another embodiment, the controller distinguishes between changes in the force sensor outputs due to occupant movement relative to the support surface and changes in the force sensor outputs due to the siderail moving between the up and down position.

The controller distinguishes between changes in the force sensor outputs due to occupant movement relative to the support surface and changes in the force sensor outputs due to changes in height of the support surface in at least one other embodiment.

The controller distinguishes between changes in the force sensor outputs due to occupant movement relative to the support surface and changes in the force sensor outputs due to changes in the position of the support surface on the litter frame in still other embodiments.

In any of the embodiments discussed herein, the plurality of force sensors may be a plurality of load cells adapted to support the litter frame.

According to still another embodiment, a person support apparatus is provided that includes a support surface, an actuator, a plurality of force sensors, and a controller. The support surface supports thereon an occupant of the person support apparatus. The actuator moves the support surface. The force sensors detect forces from a load exerted thereon. The load includes the support surface and, if present, the occupant. The controller communicates with the actuator and the force sensors. The controller causes the actuator to move the support surface when the occupant is not on the support surface and records outputs from the plurality of force sensors when the support surface moves. The controller also uses data generated from the recorded outputs to adjust subsequent outputs from the force sensors generated when the occupant is present on the support surface.

In other embodiments, the support surface includes a first section and a second section, and the actuator pivots the first section with respect to the second section about a generally horizontal pivot axis.

In some embodiments, the person support apparatus also includes a litter frame adapted to tilt with respect to a horizontal plane and to support the support surface, and the actuator tilts the litter frame and support surface. The tilting occurs about a lateral axis, in one embodiment, such that a head end of the litter frame changes its height with respect to a foot end, and occurs about a longitudinal axis in another embodiment, such that a first side of the litter frame changes its height with respect to the other side.

In still other embodiments, the actuator is adapted to change a height of the litter frame and support surface.

According to still other embodiments, the actuator is adapted to move the support surface toward or away from an end of the litter frame.

In at least some embodiments, the controller uses the outputs from the plurality of force sensors when no occupant is on the support surface to determine changes in a center of gravity of the load as the actuator moves. The controller may also use the changes in the center of gravity of the load to adjust the subsequent outputs from the force sensors generated when the occupant is present on the support surface.

The person support apparatus also includes, in some embodiments, a user input in communication with the controller. The user input prompts the controller to cause the actuator to move the support surface when the occupant is not on the support surface and to record outputs from the plurality of force sensors when the support surface moves.

Before the various embodiments disclose herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION OF THE EMBODIMENTS

Figure 1:
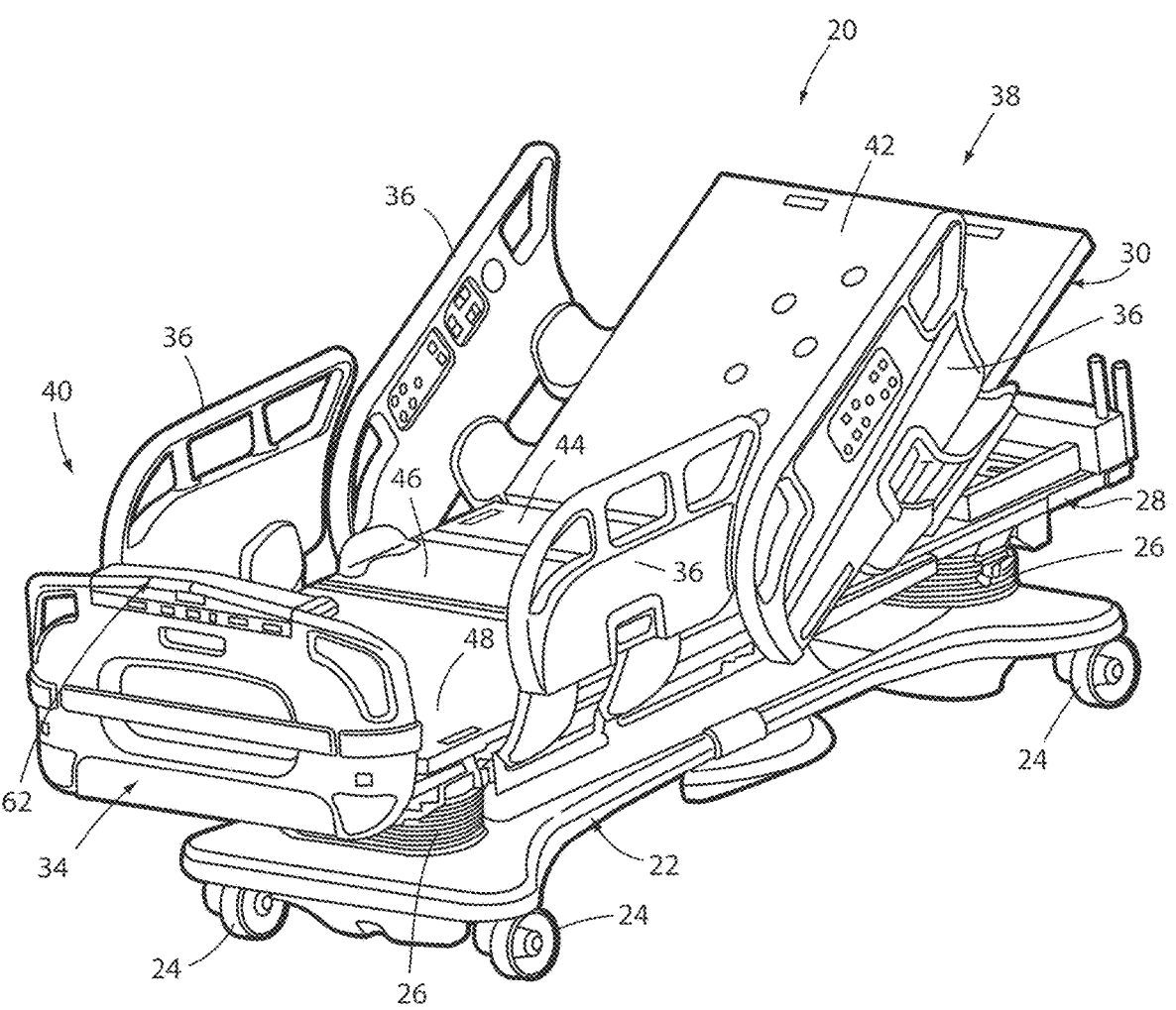
FIG. 1 is a perspective view of a person support apparatus into which one or more aspects of the present disclosure may be incorporated.

An illustrative person support apparatus 20 that may incorporate one or more aspects of the present disclosure is shown in FIG. 1. Although the particular form of person support apparatus 20 illustrated in FIG. 1 is a bed adapted for use in a hospital or other medical setting, it will be understood that person support apparatus 20 could, in different embodiments, be a cot, a stretcher, a gurney, a recliner, an operating table, a residential bed, or any other structure capable of supporting a person, whether stationary or mobile and/or whether medical or residential.

In general, person support apparatus 20 includes a base 22 having a plurality of wheels 24, a pair of lifts 26 supported on the base, a litter frame 28 supported on the lifts 26, and a support deck 30 supported on the litter frame 28. Person support apparatus 20 further includes a headboard (not shown), a footboard 34, and a plurality of siderails 36. Siderails 36 are all shown in a raised position in FIG. 1 but are each individually movable to a lower position in which ingress into, and egress out of, person support apparatus 20 is not obstructed by the lowered siderails 36.

Lifts 26 are adapted to raise and lower litter frame 28 with respect to base 22. Lifts 26 may be hydraulic actuators, electric actuators, or any other suitable device for raising and lowering litter frame 28 with respect to base 22. In the illustrated embodiment, lifts 26 are operable independently so that the tilting of litter frame 28 with respect to base 22 can also be adjusted. That is, litter frame 28 includes a head end 38 and a foot end 40, each of whose height can be independently adjusted by the nearest lift 26. Person support apparatus 20 is designed so that when an occupant lies thereon, his or her head will be positioned adjacent head end 38 and his or her feet will be positioned adjacent foot end 40.

Litter frame 28 provides a structure for supporting support deck 30, the headboard, footboard 34, and siderails 36. Support deck 30 provides a support surface for a mattress (not shown in FIG. 1), or other soft cushion, so that a person may lie and/or sit thereon. The top surface of the mattress or other cushion forms a support surface 31 for the occupant (see, e.g. FIGS. 9 and 9A). Support deck 30 is made of a plurality of sections, some of which are pivotable about generally horizontal pivot axes. In the embodiment shown in FIG. 1, support deck 30 includes a head section 42, a seat section 44, a thigh section 46, and a foot section 48. Head section 42, which is also sometimes referred to as a Fowler section, is pivotable about a generally horizontal pivot axis between a generally horizontal orientation (not shown in FIG. 1) and a plurality of raised positions (one of which is shown in FIG. 1). Thigh section 46 and foot section 48 may also be pivotable about generally horizontal pivot axes.

Support deck 30 is, in the embodiment shown in FIG. 1, movable on litter frame 28 in a longitudinal direction. That is, support deck 30 is adapted to move on litter frame 28 toward and away from head end 38 and foot end 40. In one embodiment, person support apparatus 20 is mechanically constructed such that pivoting of head section 42 about its associated horizontal pivot axis occurs simultaneously with longitudinal movement of support deck 30 along litter frame 28. More specifically, in this embodiment, support deck 30 moves longitudinally along litter frame 28 toward foot end 40 when head section 42 pivots downwardly toward a flat orientation, and support deck 30 moves longitudinally along litter frame 28 toward head end 38 when head section 42 pivots upwardly toward a raised orientation.

Figure 2:
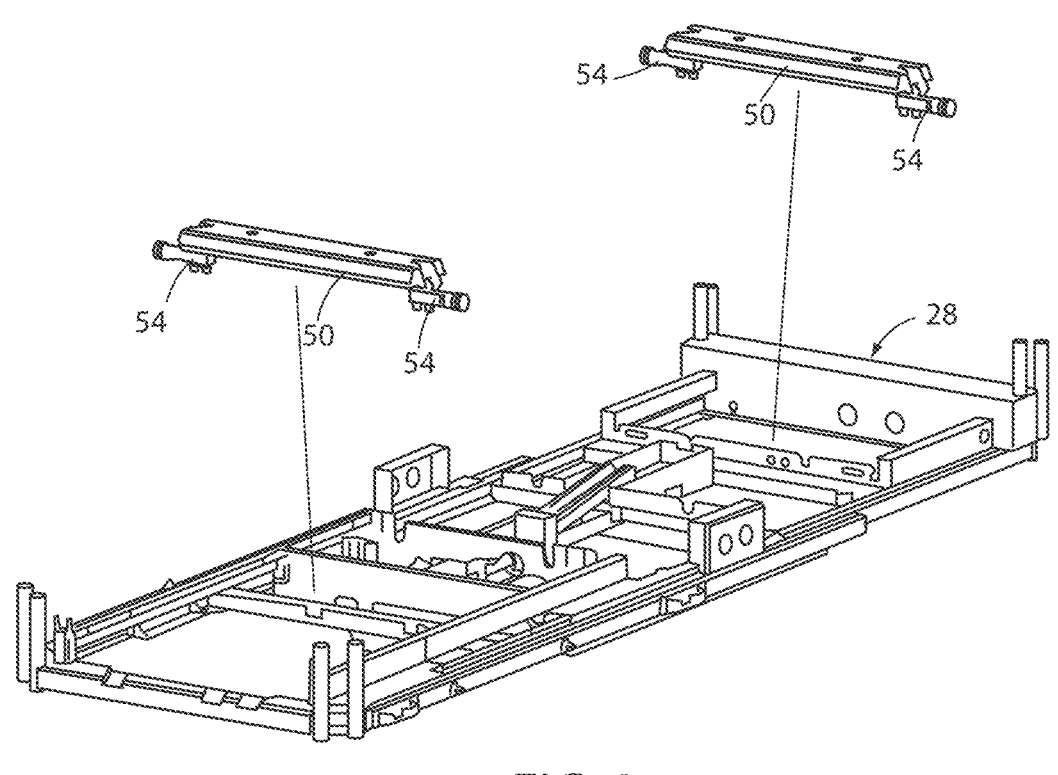
FIG. 2 is a perspective view of a litter frame of the person support apparatus of FIG. 1.

FIG. 2 illustrates in greater detail litter frame 28 separated from lifts 26 and base 22. Litter frame 28 is also shown in FIG. 2 with support deck 30 removed. Litter frame 28 is supported by two lift header assemblies 50. A first one of the lift header assemblies 50 is coupled to a top 52 (FIG. 3) of a first one of the lifts 26, and a second one of the lift header assemblies 50 is coupled to the top 52 of the second one of the lifts 26. Each lift header assembly 50 includes a pair of load cells 54. The illustrated embodiment of person support apparatus 20 therefore includes a total of four load cells 54, although it will be understood by those skilled in the art that different numbers of load cells may be used in accordance with the principles of the present disclosure. Load cells 54 are configured to support litter frame 28. More specifically, load cells 54 are configured such that they provide complete and exclusive mechanical support for litter frame 28 and all of the components that are supported on litter frame 28 (e.g. support deck 30, footboard 34, the headboard, siderails 36, etc.). Because of this construction, load cells 54 are adapted to detect the weight of not only those components of person support apparatus 20 that are supported by litter frame 28 (including litter frame 28 itself), but also any objects or persons who are wholly or partially being supported by support deck 30. The outputs of load cells 54 are fed into an exit detection system described in greater detail below.

Figure 3:
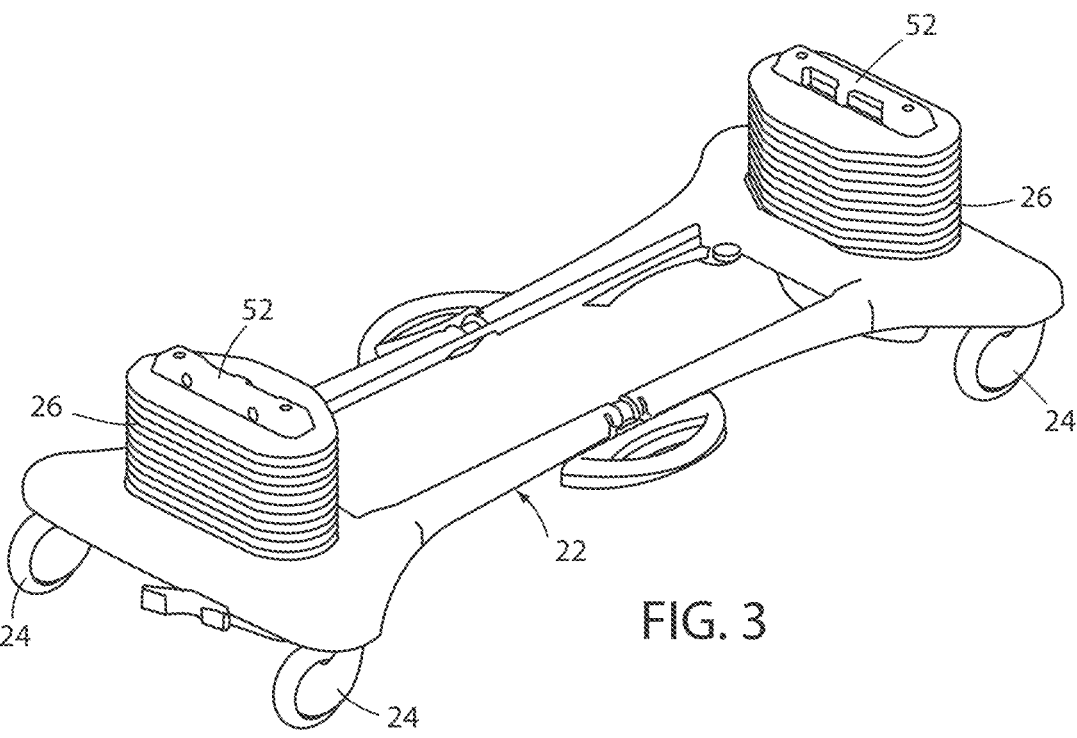
FIG. 3 is a perspective view of a base of the person support apparatus of FIG. 1.

As shown in FIGS. 1-3, the mechanical construction of person support apparatus 20 is the same as, or nearly the same as, the mechanical construction of the Model 3002 S3 bed manufactured and sold by Stryker Corporation of Kalamazoo, Michigan. This mechanical construction is described in greater detail in the Stryker Maintenance Manual for the MedSurg Bed, Model 3002 S3, published in 2010 by Stryker Corporation of Kalamazoo, Michigan, the complete disclosure of which is incorporated herein by reference. It will be understood by those skilled in the art that person support apparatus 20 can be designed with other types of mechanical constructions, such as, but not limited to, those described in commonly assigned, U.S. Pat. No. 7,690,059 issued to Lemire et al., and entitled HOSPITAL BED; and/or commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosures of both of which are also hereby incorporated herein by reference. The mechanical construction of person support apparatus 20 may also take on forms different from what is disclosed in the aforementioned references.

Figure 4:
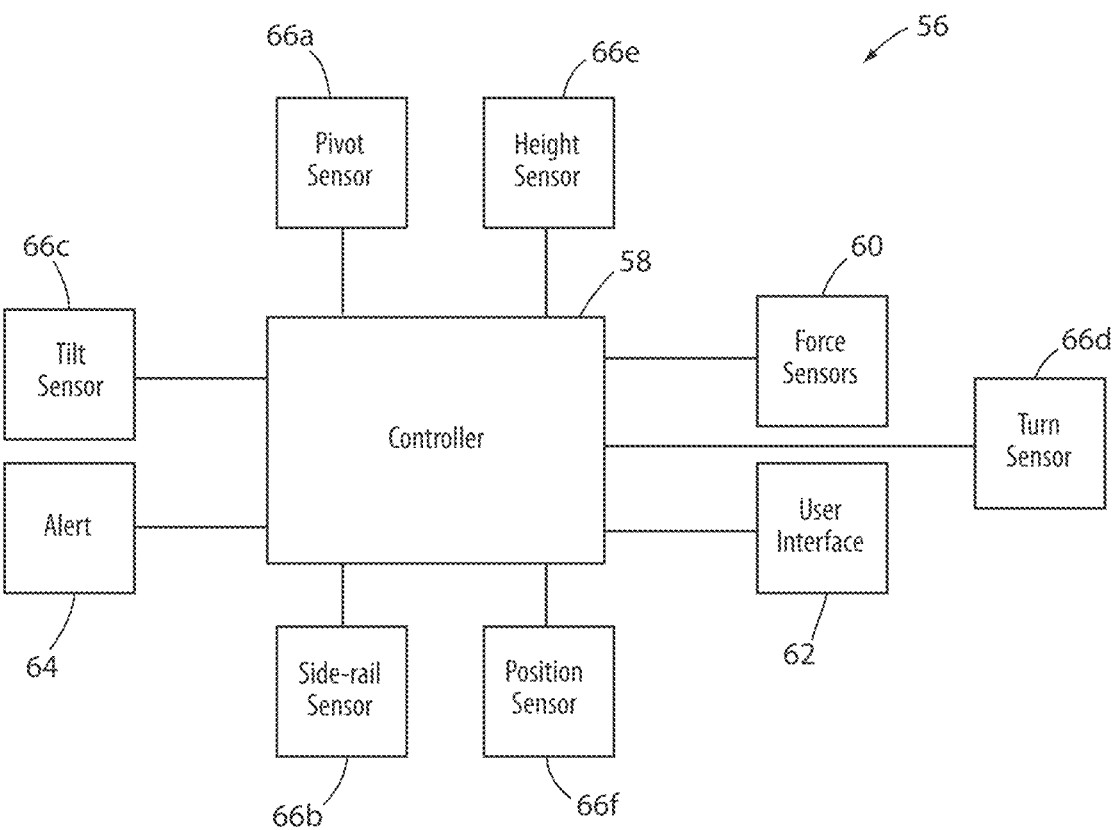
FIG. 4 is a diagram one embodiment of an exit detection system that may be incorporated into a person support apparatus such as, but not limited to, the person support apparatus of FIG. 1.

As shown more clearly in FIG. 4, person support apparatus 20 includes an exit detection system 56 that is adapted to determine when an occupant, such as, but not limited to, a patient, of person support apparatus 20 is likely to exit person support apparatus 20. More specifically, exit detection system 56 is adapted to determine when an occupant is likely to leave prior to the occupant actually leaving, and to issue an alert and/or notification to appropriate personnel so that proper steps can be taken in response to the occupant's imminent departure in a timely fashion. The particular structural details of exit detection system 56 can vary widely. In the embodiment shown in FIG. 4, exit detection system 56 includes a controller 58, a plurality of force sensors 60, a user interface 62, an alert 64, and a plurality of sensors 66. More specifically, the sensors 66 include a pivot sensor 66a, a siderail sensor 66b, a tilt sensor 66c, a turn sensor 66d, a height sensor 66e, and a position sensor 66f.

Force sensors 60 are adapted to detect downward forces exerted by an occupant of support deck 30. Thus, when an occupant is positioned on support deck 30 and substantially still (i.e. not moving in a manner involving accelerations that cause forces to be exerted against support deck 30), force sensors 60 will detect the weight of the occupant (as well as the weight of any components of person support apparatus 20 that are supported-directly or indirectly—by force sensors 60). In at least one embodiment, force sensors 60 are the same as, and positioned in the same locations as, load cells 54, as shown in FIG. 2. It will be understood by those skilled in the art, however, that force sensors 60 may be implemented as other types of sensors, such as, but not limited to, linear variable displacement transducers and/or any one or more capacitive, inductive, and/or resistive transducers that are configured to produce a changing output in response to changes in the force exerted against them.

Pivot sensor 66a (FIG. 4), in one embodiment, detects a pivot angle 70 (FIG. 6A) between head section 42 a plane generally defined by litter frame 28. In some embodiments, pivot sensor 66a does not directly measure pivot angle 70 of head section 42, but instead indirectly measures angle 70 by measuring the angle of another component of person support apparatus 20 whose angular orientation has a known relationship with angle 70, or by measuring the position of another component of person support apparatus 20 whose position has a known relationship with angle 70.

Figures 7, 7A, 7B:
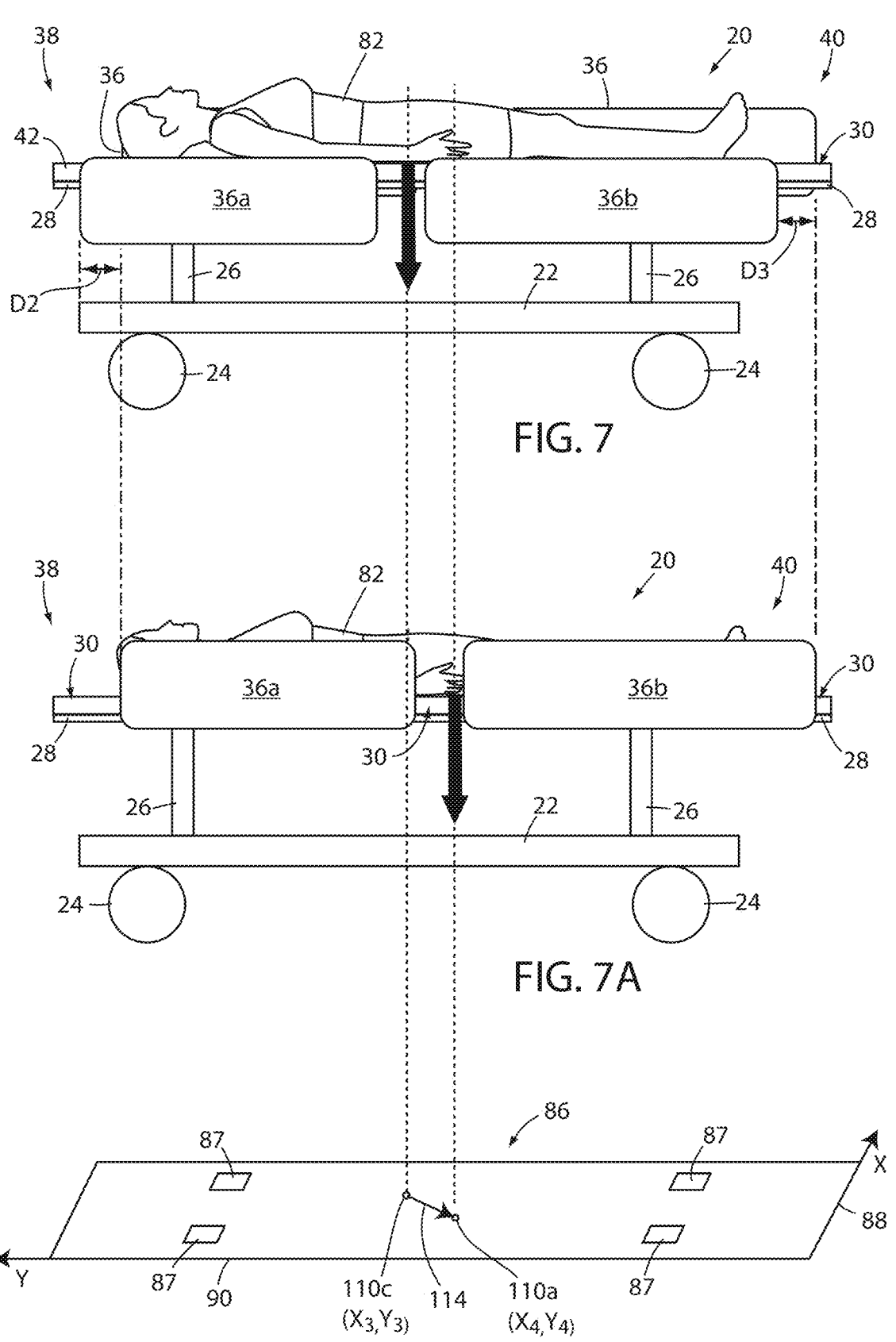
FIG. 7 is a side elevation diagram of a person support apparatus that shows a center of gravity of a load when a pair of siderails are in a down position.
FIG. 7A is a side elevation diagram of the person support apparatus of FIG. 7 that shows the center of gravity when the pair of siderails are moved to an up position.
FIG. 7B is a perspective view of a planar coordinate system that illustrates changes to the center of gravity caused by the siderail movement between FIGS. 7 and 7A.

Each siderail sensor 66b is adapted to detect whether the siderail 36 it is associated with is in an up position or a down position. Two of the siderails 36 are illustrated in FIG. 7 in the down position (and two are illustrated in the up position in FIG. 7), while all of the siderails 36 are illustrated in the up position in FIG. 7A. In some embodiments, siderails 36 are also movable to one or more intermediate positions. In those embodiments, siderails sensors 66b are also adapted to detect if their associated siderail 36 is in an intermediate position. In the embodiment of person support apparatus 20 shown in FIG. 1, there are four siderails 36 and thus four siderail sensors 66b, each of which senses the position of one of the four siderails 36.

Tilt sensor 66c detects a tilt angle 72 (FIG. 8A) of litter frame 28 with respect to horizontal. In one embodiment, tilt sensor 66c measures this angle directly. In other embodiments, tilt sensor 66c comprises two sensors that detect the distance which each of lifts 26 are extended and circuitry that calculates the tilt angle of litter frame 28 with respect to horizontal from these two distances. In still other embodiments, tilt sensors 66c takes on other forms.

Figures 8, 8A, 8B:
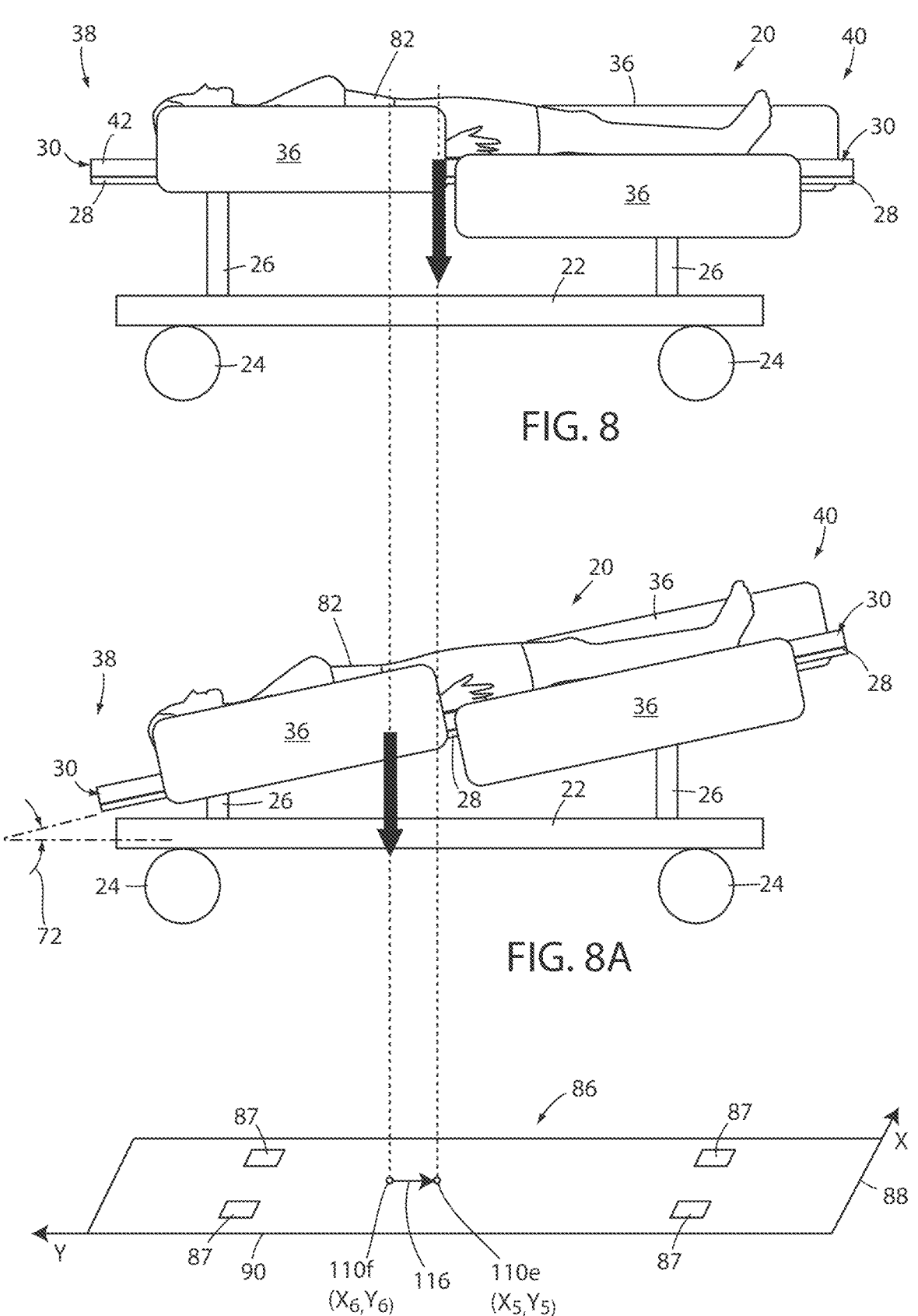
FIG. 8 is a side elevation diagram of a person support apparatus that shows a center of gravity of a load when a litter frame of the person support apparatus is horizontal.
FIG. 8A is a side elevation diagram of the person support apparatus of FIG. 8 that shows the center of gravity when the litter frame has been tilted.
FIG. 8B is a perspective view of a planar coordinate system that illustrates changes to the center of gravity caused by the tilting movement between FIGS. 8 and 8A.

Although tilt angle 72 is illustrated in FIG. 8A as being defined with respect to tilting that occurs about a lateral pivot axis (i.e. head end 38 changes its height with respect to foot end 40), it will be understood that tilt angle 72, in some embodiments, is configured to measure a tilt angle 72 of litter frame 28 that changes as a result of tilting about a longitudinal axis (i.e. a first side of litter frame 28 changes its height with respect to the second side).

Turn sensor 66d detects a turn angle 74 (FIG. 9A) of a turning mechanism, such as a powered mattress 76 having one or more inflatable turning bladders, that is used to turn an occupant of person support apparatus 20. Turn sensor 66d is, in at least one embodiment, positioned inside of mattress 76 and measures turn angle 74 directly. In other embodiments, turn sensor 66d measures one or more inflation pressures of one or more bladders inside of mattress 76 and estimates turn angle 74 based upon the one or more measured inflation pressures.

Height sensor 66e detects either an absolute or relative height 78 (FIG. 7A) of litter frame 28. More specifically, in one embodiment, height sensor 66e detects how far each lift 26 has extended from its lowest position. In another embodiment, height sensor 66e detects how high one or more points on litter frame 28 (or any component of person support apparatus 20 non-movably coupled to litter frame 28) is with respect to a reference (e.g. a floor, base 22, etc.).

Position sensor 66f detects the longitudinal position of support deck 30 relative to litter frame 28. That is, as noted previously, support deck 30 is longitudinally movable, in some embodiments, with respect to litter frame 28 in a direction indicated by the arrow identifying distance D1 in FIG. 6A. In some embodiments, person support apparatus 20 is constructed such that the longitudinal position of support deck 30 relative to litter frame 28 is directly correlated to pivot angle 70. In such embodiments, position sensor 66f pivot angle sensor 66a may be one and the same. In still other embodiments, person support apparatus 20 may be constructed such that the longitudinal position of support deck 30 relative to litter frame 28 is directly correlated to the position and/or orientation of some other component of person support apparatus, in which case position sensor 66f may be configured to measure the position of support deck 30 indirectly by measuring the position or orientation of the other component.

All of the sensors 66 are in communication with controller 58 (FIG. 4). Controller 58 is constructed of any electrical component, or group of electrical components, that are capable of carrying out the functions described herein. In many embodiments, controller 58 is a conventional microcontroller, although not all such embodiments need include a microcontroller. In general, controller 58 includes any one or more microprocessors, microcontrollers, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by controller 58 in carrying out the functions described herein, as well as the data necessary for carrying out these functions, are stored in a memory (not labeled) accessible to controller 58.

Controller 58 is also in communication with user interface 62. User interface 62 is implemented in the embodiment shown in FIG. 1 as a control panel having a lid (flipped down in FIG. 1) underneath which is positioned a plurality of controls. The controls-which may be buttons, dials, switches, or other devices-allows a user to control various aspects of exit detection system 56. User interface 62 may also include a display for displaying information regarding exit detection system 56. Although FIG. 1 illustrates user interface 62 mounted to footboard 34, it will be understood that user interface 62 can be positioned elsewhere, and/or that one or more additional user interfaces can be added to person support apparatus 20 in different locations, such as the siderails 36, for controlling various aspects of exit detection system 56.

In one embodiment, user interface 62 includes a control that enables a user to turn exit detection system 56 on and off, as well as allowing a user to select different sensitivity levels or zones which are used for triggering an exit alert, as will be discussed in greater detail below. In at least some embodiments, the controls also allow a user to configure the alerting features of exit detection system 56, including choosing from amongst the different types of alerts that can be issued by exit detection system 56. Such types include local alerts (issued at person support apparatus 20), remote alerts (issued at a remote location, such as a nurse's station, hallway light, or to mobile communication devices carried by personnel), audio alerts, visual alerts, and/or any combinations of these.

Controller 58 of exit detection system 56 is adapted to determine the center of gravity of whatever load is applied to force sensors 60. In other words, exit detection system 56 determines the center of gravity of the combined weight of an occupant, mattress, and/or any objects that are positioned on support deck 30 or litter frame 28, as well as those components of person support apparatus 20 whose weight is supported by force sensors 60 (e.g. litter frame 28, support deck 30, siderails 36, etc.) In one embodiment, exit detection system 56 determines this center of gravity using the system and method disclosed in commonly assigned U.S. Pat. No. 5,276,432 issued to Travis and entitled PATIENT EXIT DETECTION MECHANISM FOR HOSPITAL BED, the complete disclosure of which is incorporated herein by reference. In other embodiments, other algorithms may be used.

Exit detection system 56 differs from the exit detection system disclosed in the aforementioned U.S. Pat. No. 5,276, 432 patent in multiple manners. One difference is that exit detection system 56 is configured to distinguish between detected changes in the center of gravity of the load that are due to the occupant moving with respect to support surface 31, and changes in the detected center of gravity of the load that are due to other factors. Such other factors include, but are not limited to, pivoting of one or more sections of deck 30; tilting of litter frame 28; longitudinal movement of support deck 30 relative to litter frame 28; movement of one or more siderails 36 from an up position to a down positions, or vice versa; changes in height of litter frame 28; and/or therapeutic turning of the occupant by a turning device built into mattress 76 or otherwise positioned on top of support deck 30. Stated alternatively, exit detection system 56 is configured to determine how much, if any, of the changes in the outputs of force sensors 60 is due to patient movement relative to support surface 31 and how much, if any, of the changes in the outputs of force sensors 60 is due to other factors. Exit detection system 56 compensates the readings it obtains from force sensors 60 in order to account for these other factors. If the compensated outputs of the force sensors 60 meet one or more criteria, as will be discussed in greater detail below, system 56 issues an alert.

Figure 5:
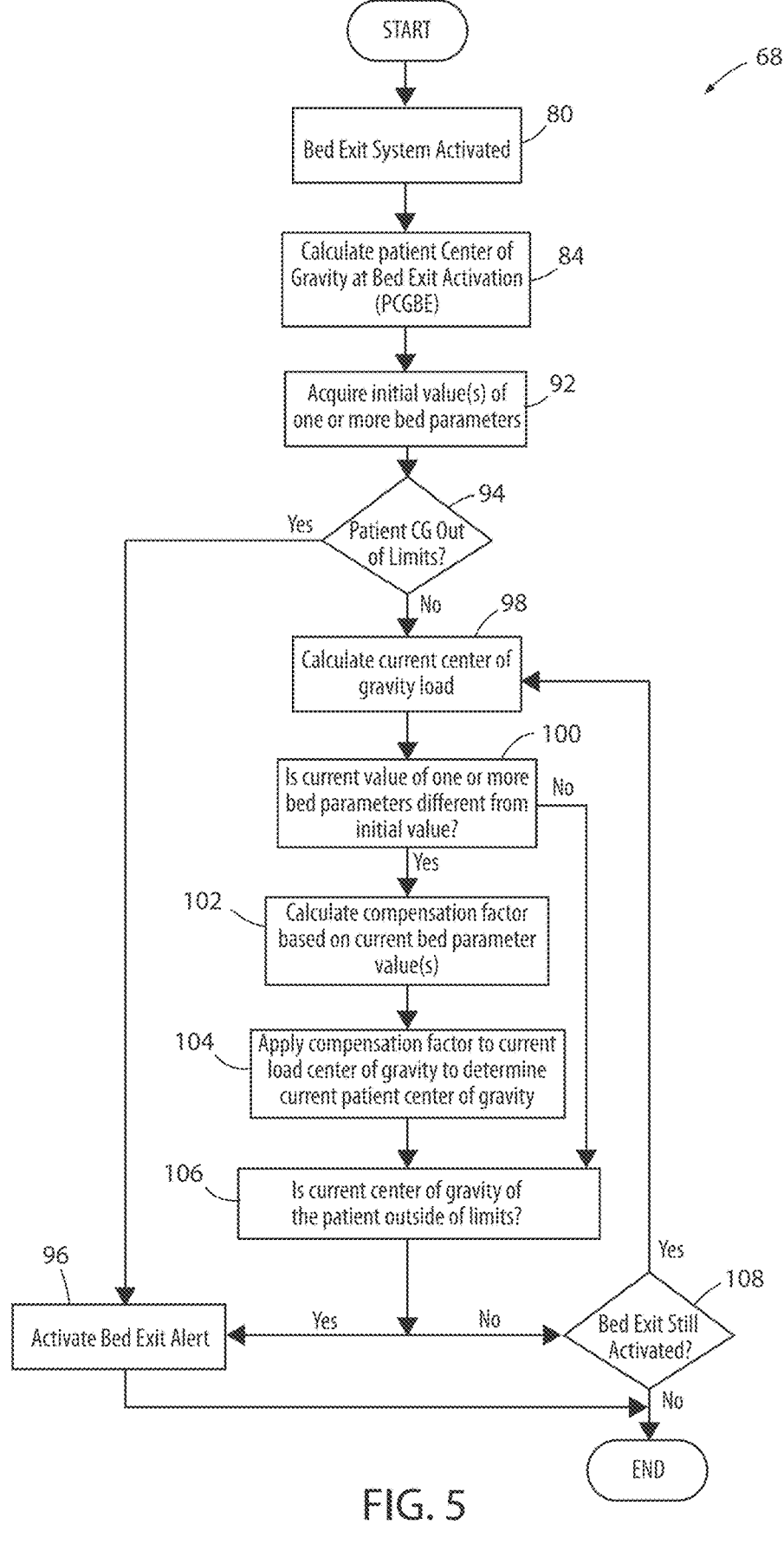
FIG. 5 is a flowchart of one embodiment of an exit detection algorithm that is carried out by the exit detection system of FIG. 4.

One example of an exit detection algorithm 68 that is carried out, in at least one embodiment, by controller 58 of exit detection system 56 is illustrated in FIG. 5. Exit detection algorithm 68 begins at an initial step 80 when exit detection system 56 is armed, such as by a user manipulating one or more controls on user interface 62. After being armed at step 80, controller 58 proceeds to step 84 where it calculates an initial center of gravity of the occupant of person support apparatus 20. This calculation is performed using known mathematical techniques for computing a center of gravity, as well as knowledge of the relative positions of the force sensors 60. Although other coordinate systems may be used, controller 58 computes the center of gravity using a planar coordinate system 86 (FIG. 6B) having an x-axis 88 that is generally parallel to the foot end 40 of support deck 30 and a y-axis 90 that is generally parallel to a side of support deck 30. Other coordinate systems can be used. Regardless of which coordinate system is used, controller 58 knows the location of force sensors 60 in the particular coordinate system that is used. In the example shown in FIG. 6B, force sensors 60 are shown in known locations 87.

After determining the occupant's center of gravity at step 84, controller 58 proceeds to step 92 where it determines the initial value of one or more parameters of person support apparatus 20. More specifically, in the embodiment illustrated in FIG. 5, controller 58 determines the following values at step 92: a current value of pivot angle 70; a current value of tilt angle 72, a current value of turn angle 74, a current value corresponding to the current relative longitudinal position of support deck 30 on litter frame 28, a current value of height 78, and a current value indicating the current position of each siderail 36 (up, down, or intermediate). It will be understood by those skilled in the art that, in other embodiments, algorithm 68 is modified to determine less than or more than all six of these values. Indeed, in other embodiments, controller 58 determines any one or more of these six values at step 92, or still other values.

After completing step 92, controller 58 moves onto step 94 (FIG. 5) where it determines whether the center of gravity of the occupant determined at step 84 is outside of a predefined zone. The predefined zone, in one embodiment, is defined in coordinate system 86 and is the trigger controller 58 uses to determine whether or not to issue an exit alert, in at least one embodiment. Although other types of zones may be used, in the illustrated embodiment, the zone is generally rectangular or square shaped. If the occupant's center of gravity it outside of the zone, controller 58 issues an alert at step 96. If the occupant's center of gravity is not outside of the zone, controller 58 proceeds to step 98.

It will be understood that, in at least some embodiments, exit detection system 56 is configured to allow a user to select which zone will be used by controller 58 when determining whether to issue an alert or not (such as at step 94). In some embodiments, person support apparatus 20 includes three predefined zones and is adapted to allow a user to select which one of these three zones is to be used at a given time via user interface 62. In other embodiments, different numbers of zones are used.

In still other embodiments, it will be understood that—when multiple zones are selectable by a user—the boundaries of the different zones may be defined in different manners. For example, in one embodiment, the zone having the smallest area (in coordinate system 86) has its boundaries defined using the patient's center of gravity reading taken at step 84. That is, the smallest zone is centered at whatever location the person's center of gravity is initially located, as determined at step 84. The zone having the largest area is defined, in at least one embodiment, without regard to the occupant's initial location, but instead has fixed values in coordinate system 86. For example, in one embodiment, the zone with the largest area has its edges located just inwardly from the outer edges of support deck 30. Other manners of defining the zone boundaries may also be used.

Also, in at least one embodiment, the definition of one or more zones is dynamic. For example, in at least one embodiment, the shape and/or boundaries of a zone change based upon whether or not a siderail is in the up position or the down position. If a siderails is in an up position, it is less likely that an occupant of person support apparatus 20 will exit therefrom by climbing over that siderail. Accordingly, controller 58 may use, in that situation, a zone that allows the occupant's center of gravity to approach more closely to the up siderail than if the siderail were in a down position before issuing an alarm. If the siderail is moved to a lower position, the zone is switched to include a more restricted boundary—the more restricted boundary representing the fact that, with the siderail lowered, it is easier for an occupant to exit support deck 30 in the area of the lowered siderail. Still other factors besides the status of the siderails may cause the zone used by controller 58 to dynamically change during monitoring of the movement of the occupant.

Regardless of the definition of the zone, and regardless of whether it is dynamic or not, controller 58 proceeds to step 98 if it determines at step 94 that the occupant's center of gravity (as determined at step 84) is not outside of the currently in-use zone. At step 98, controller 58 calculates the center of gravity of the load detected by force sensors 60. As will be discussed below, this center of gravity may or may not correspond to the center of gravity of the occupant, depending upon what movement may have occurred between the center of gravity calculation at step 84 and the center of gravity calculation at step 98. That is, it is possible that the center of gravity of the load sensed by force sensors 60 may have changed during the time between steps 84 and 98 without the occupant moving relative to support surface 31 due to, for example, one or more components of the person support apparatus 20 having moved. Alternatively, it is possible that the center of gravity of the load sensed by force sensors 60 at step 98 corresponds to the patient's center of gravity (whether it has moved or not). Controller 58 resolves whether the center of gravity reading taken at step 98 is the result of patient movement relative to support surface 31 or some other factors by following steps 100-106, as will now be discussed.

After calculating the center of gravity of the load sensed by force sensors 60 at step 98, controller 58 proceeds to step 100 (FIG. 5). At step 100, controller 58 determines whether any of the initial values acquired at step 92 have changed during the interim between step 92 and step 100. More specifically, in the illustrated embodiment, controller 58 determines at step 100 whether any of the following values have changed: the value of pivot angle 70, the position value (e.g. up, down, and/or intermediate) for each of the siderails 36, the value of tilt angle 72, the value of turn angle 74, the height value 78, and the position value corresponding to the current relative longitudinal position of support deck 30 on litter frame 28. Controller 58 determines these values at step 100 based upon readings from pivot sensor 66a, siderail sensor 66b, turn sensor 66c, tilt sensor 66d, height sensor 66e, and position sensor 66f, respectively.

If none of these values have changed since the values were initially taken at step 92, controller 58 proceeds to step 106. At step 106, controller 58 compares the center of gravity reading taken at step 98 to the zone. Because none of the values have changed at step 100, the center of gravity reading taken at step 98 corresponds to the center of gravity of the occupant (i.e. any changes in the center of gravity are due to occupant movement relative to support surface 31, and not due to movement of one or more components of person support apparatus 20). Controller 58 issues an exit alert at step 96 if it determines at step 106 that the center of gravity reading taken at step 98 is outside of the zone (the same zone examined in step 94). Controller 58 does not issue an exit alert if it determines at step 106 that the center of gravity reading taken at step 98 lies inside the zone. In this latter case, controller 58 then proceeds to step 108, where it checks to see if exit detection system 56 is still armed or not. If not, algorithm 68 ends. If so, however, controller 58 returns to step 98 where it takes new readings from force sensors 60 and calculates a new center of gravity reading based on those new readings. Control then follows in the same manner and sequence as described.

If controller 58 determines at step 100 that one or more of the initial values (from step 92) have changed, it proceeds to a step 102, where it determines one or more compensation factors that correspond to the changed values. That is, for every value that has changed, controller 58 computes a compensation factor at step 102. Thus, for example, if pivot angle 70 and height 78 are both different at step 100 than they were initially at step 92, controller 58 computes a pivot angle compensation factor and a height compensation factor. Further explanation of these compensation factors is provided below with respect to FIGS. 6-9B. In general, controller 58 calculates at step 102 one or more compensation factors that provide an estimate of how much the center of gravity reading taken at step 98 has been influenced by factors other than the occupant moving relative to support deck 30. Thus, as one example, if a siderail 36 has been moved to a new position (and that new position changes the overall distribution of weight sensed by force sensors 60), controller 58 calculates at step 102 an estimate of how much the weight distribution has been changed by the movement of that siderail. Similar calculations are made for any changes in pivot angle 70, tilt angle 72, turn angle 74, height 78, and/or the longitudinal position of support deck 30 relative to litter frame 28, as will be discussed in greater detail below.

After the one or more compensation factors are calculated at step 102, controller 58 moves to step 104 where it applies the compensation factor(s) to the center of gravity computed at step 98. The result is a center of gravity calculation that has substantially eliminated changes in the center of gravity due to movement of one or more components of person support apparatus 20, or other effects that are not the result of the occupant changing his or her weight distribution relative to support deck 30 or support surface 31. Consequently, the compensated center of gravity calculation made at step 104 corresponds substantially to the occupant's center of gravity. Controller 58 then proceeds to step 106 where it determines whether the occupant's center of gravity (i.e. the compensated center of gravity calculated at step 104) is inside or outside of the zone that defines the exit alert conditions. If it is outside the zone, an alert is issued at step 96. If it inside the zone, no alert is issued and—to the extent exit detection system 56 has not been shut off—control returns to step 98 where another center of gravity reading is taken.

The exit alert issued at step 96 may take on any suitable form. In one embodiment, the exit alert includes an aural alert issued from a speaker, buzzer, or other sound-generating device on person support apparatus 20 that is under the control of exit detection system 56, or in communication with exit detection system 56. In another embodiment, controller 58 also issues a remote alert, such as at a nurses' station, or other location, where one or more caregivers who may be assigned to care for the occupant of person support apparatus 20 are located. The remote alert is carried out via any suitable interface and/or communication link, such as, but not limited to, a nurse-call cable, a wireless communication channel (e.g. Wi-Fi, Bluetooth, and/or ZigBee). In still another embodiment, person support apparatus 20 is configured to allow a user to choose whether the exit alert is local and/or remote, as well as to choose characteristics of the exit alert (e.g. the volume and/or tone of an aural exit alert). After issuing the exit alert, controller 58 ends exit detection algorithm 68 until it is once again re-started in response to a user's command.

In the embodiment illustrated in FIG. 5, the compensation factors that may be computed at step 102 include the following: (1) a head section angle compensation factor, (2) a siderail compensation factor, (3) a tilt compensation factor, (4) a height compensation factor, (5) a support deck position compensation factor, and (6) a turn compensation factor. It will be understood by those skilled in the art that fewer or greater numbers of compensation factors may be computed at step 102 in different embodiments. In general, controller 58 calculates a compensation factor at step 102 for each of the values that have changed since step 92. However, it will be understood by those skilled in the art that some values may be combined to calculate a single compensation factor. Thus, for example, in some person support apparatuses, pivot angle 70 changes in unison with the longitudinal position of support deck 30 relative to litter frame 28, and controller 58 can be modified to calculate a single compensation factor that takes into account both of these changes with a single factor. Other variations may also be implemented.

Figures 6, 6A, 6B:
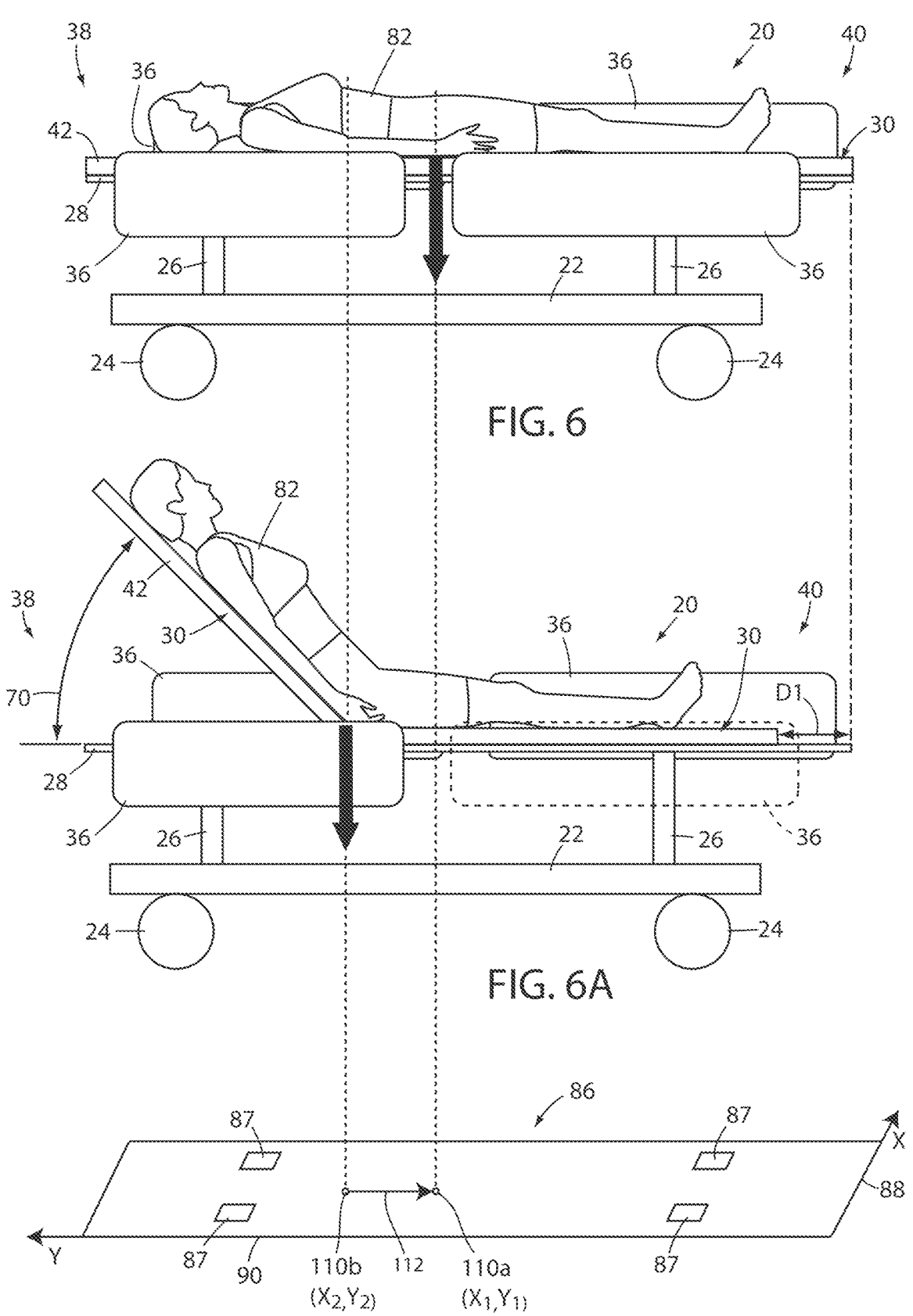
FIG. 6 is a side elevation diagram of a person support apparatus that shows a center of gravity of a load when the support deck is flat.
FIG. 6A is a side elevation diagram of the person support apparatus of FIG. 6 that shows the center of gravity when a head section of the support deck has been raised.
FIG. 6B is a perspective view of a planar coordinate system that may be used by the algorithm of FIG. 5 to compute the load's center of gravity and that also illustrates changes to the center of gravity caused by the movement between FIGS. 6 and 6A.

FIGS. 6-6B illustrate in greater detail one manner in which a combined head section angle and support deck position compensation factor is computed. As shown in FIG. 6, occupant 82 is lying on support deck 30 in the same position relative to support deck 30 as in FIG. 6A. That is, the occupant 82 is lying on his or her back and has his or her torso, legs, head, and arms in contact with support deck 30 (or a mattress positioned on top of support deck 30). When person support apparatus 20 is in the flat orientation shown in FIG. 6 (i.e. pivot angle 70 is substantially zero), exit detection system 56 detects a center of gravity 110a that is located in coordinate system 86 at location $(X_1, Y_1)$. However, when head section 42 is pivoted upwardly to the orientation shown in FIG. 6A, exit detection system 56 detects a center of gravity 110b that has moved to location $(X_2, Y_2)$. A vector 112 extends between these two points in FIG. 6B and corresponds to the compensation factor that is used by exit detection system 56 when head section 42 pivots upwardly the amount shown in FIG. 6A and support deck 30 changes its longitudinal position relative to litter frame 28.

The difference between centers of gravity 110*a* and 110*b* is due to several factors. One factor is the change in movement of support deck 30 relative to litter frame 28. Specifically, in the example shown in FIGS. 6 and 6A, person support apparatus 20 is constructed such that support deck 30 automatically changes its longitudinal position relative to litter frame 28 as head section 42 pivots. Thus, as shown in FIG. 6A, support deck 30 has moved toward head end 38 of person support apparatus 20 a distance D1 relative to its position in FIG. 6. This positional change shifts the center of gravity of the load detected by force sensors 60. Another factor that shifts the location of the center of gravity detected by force sensors 60 is the movement of the occupant's torso and head, as well as head section 42, upward. These combined factors are the primary reason for the difference between the two centers of gravity 110*a* and 110*b* shown in FIG. 6B.

The magnitude of vector 112, and thus the magnitude of the compensation factor, changes as pivot angle 70 changes. The direction of vector 112, and thus the magnitude of the compensation factor, may also change, in some cases, as pivot angle 70 changes, although this is not typical because there is substantially no change or movement in the x-direction of coordinate system 86 between the configurations of FIGS. 6 and 6A. The amount by which vector 112 changes will typically vary for different occupants 82 who have different weights, or who are positioned differently on support deck 30. Vector 112 will also vary for differently constructed person support apparatuses that have different geometries, materials, and/or constructions of support deck 30 and/or litter frame 28. Exit detection system 56 takes into account these variations by relying upon, in at least one embodiment, empirical data that is gathered from multiple occupants of different weight. More specifically, empirical data is gathered for the particular person support apparatus 20 in which exit detection system 56 is implemented that shows the relationship between changes in the detected center of gravity when head section 42 pivots and the occupant does not move relative to support deck 30.

In at least one embodiment, the empirical data is gathered and categorized by weight classes of the multiple occupants. As an example, empirically gathered data may be classified into the following weight classes: occupants under 100 pounds, occupants between 100-150 pounds, occupants between 150 and 200 pounds; occupants between 200 and 300 pounds, and occupants between 300 and 500 pounds. Different numbers of weight classes can be used and/or different demarcations between the weight classes can be used. The empirically gathered data is averaged, or otherwise combined, for all occupants within each weight class. The result of the data is that, for each given weight class, an estimate is provided of the amount by which the detected center of gravity changes for each change in pivot angle 70. This data may be stored in a memory accessible to controller 58, or it may be further processed to define one or more formulas that enable controller 58 to calculate an estimate of the change in the center of gravity for a given occupant weight and a given pivot angle change 70. Regardless of whether or not the data is stored or a formula is used, controller 58 determines a compensation factor (e.g. vector 112) based upon the occupant's weight (e.g. which weight class he/she is in) and the amount by which pivot angle 70 has changed.

The occupant's weight is determined by a user entering this data into a memory accessible to controller 58 using user interface 62, in one embodiment. In another embodiment, exit detection system 56 is configured to detect the occupant's weight, either automatically or via one or more inputs from a user. One manner in which exit detection system 56 can be configured to automatically detect the occupant's weight is described in greater detail in commonly assigned U.S. patent application Ser. No. 14/212,367 filed Mar. 14, 2014 by inventors Michael Joseph Hayes et al. and entitled PATIENT SUPPORT APPARATUS WITH PATIENT INFORMATION SENSORS, the complete disclosure of which is hereby incorporated herein by reference. Exit detection system 56 can therefore utilize and/or combine algorithm 68, or any of its modifications, with any of the features and/or algorithms of the exit detection system disclosed in the aforementioned Ser. No. 14/212,367 patent application.

In the embodiment of person support apparatus 20 shown in FIGS. 6 and 6A, as noted previously, the movement of support deck 30 relative to litter frame 28 is tied to the pivoting of head section 42 in a fixed manner. Thus, exit detection system can use pivot angle 70 as a proxy for indicating both pivot angle 70 and the position of support deck 30 relative to litter frame 28, and it is not necessary to compute a separate compensation factor for the changing longitudinal position of support deck 30 relative to litter frame 28. Indeed, in this configuration of person support apparatus 20, it is not necessary to include position sensor 66*f* in exit detection system 56 because the position of support deck 30 relative to litter frame 28 is tied directly to pivot angle 70. A single vector 112 compensates for changes in the detected center of gravity due to both changes in the pivot angle 70 and changes in the relative position of support deck 30 to litter frame 28.

It will be understood, however, that exit detection system 56 can be incorporated into person support apparatuses 20 in which the longitudinal movement of support deck 30 relative to litter frame 28 can be carried out independently of any pivoting of head section 42. In such embodiments, exit detection algorithm 68 computes a separate compensation vector for changes in pivot angle 70 and a separate compensation vector for changes in the position of support deck 30 relative to litter frame 28. Each of the compensation vectors are based, in at least one embodiment, on empirically gathered data from multiple occupants of different weight. More specifically, two sets of empirical data are gathered. The first set indicates how much the center of gravity of the load detected by exit detection system 56 changes—for occupants of different weight—in response to only pivot angle 70 changing. The second set indicates how much the center of gravity of the load detected by exit detection system 56 changes—for occupants of different weight—in response to only the longitudinal position of support deck 30 changing relative to litter frame 28. In other words, the second set of data is gathered for different values of distance D1 (FIG. 6A).

Controller 58 then examines at step 100 whether pivot angle 70 has changed and whether or not the position of support deck 30 relative to litter frame 28 has changed. If only one of these has changed, controller 58 applies the appropriate compensation vector that was created from the corresponding set of empirical data. If both have changed, then controller 58 applies both compensation vector based on both sets of empirical data. Controller 58 determines the correct pivot angle compensation factor by using the first set of empirical data (or a formula based thereon) that corresponds to the change in pivot angle 70 (as detected by pivot sensor 66*a*) and the weight (or weight class) of the current occupant. Controller 58 determines the correct support deck longitudinal position compensation factor by using the second set of empirical data (or a formula based thereon) that corresponds to the change in longitudinal position of support deck 30 relative to litter frame 28 (as detected by position sensor 66*f*) and the weight (or weight class) of the current occupant. If any other values have changed at step 100, controller 58 also determines compensation factors for those other values, as discussed in greater detail below.

FIGS. 7-7B illustrate in greater detail one manner in which a siderail position compensation factor is computed. As shown in FIG. 7, occupant 82 is lying on support deck 30 in the same position relative to support deck 30 as in FIG. 7A. The difference between FIGS. 7 and 7A is that, in FIG. 7, a right head siderail 36*a* and a right foot siderail 36*b* are in a lowered position, while in FIG. 7A the siderails 36*a* and 36*b* are in the raised position. Further, as can be seen from a comparison of FIGS. 7 and 7A, siderails 36*a* and 36*b* are constructed such that they move a horizontal distance D2 and D3, respectively, when switching from their lowered position to their raised position. This horizontal change in their location changes the distribution of the load sensed by force sensors 60 because the siderails 36 are supported on litter frame 28 (which is, in turn, supported on load cells 54, or some other type of force sensors 60).

As a result of the horizontal movement of siderails 36 when changing between the raised and lowered positions, exit detection system 56 will detect a center of gravity 110*c* at location (X$_3$, Y$_3$) when siderails 36*a* and 36*b* are in their lowered position (FIG. 7), and will detect a center of gravity 110*d* at location (X$_4$, Y$_4$) when siderails 36*a* and 36*b* are in their raised position (FIG. 7A). A vector 114 extends between centers of gravity 110*c* and 110*d* in FIG. 7B and corresponds to the compensation factor that is used by exit detection system 56 when both siderails 36*a* and 36*b* change their position. Because each of the siderails 36 are movable independently of each other in person support apparatus 20, it will be understood by those skilled in the art that individual compensation factors are computed for each siderail and then added together. The vector 114 shown in FIG. 7B is thus the cumulative sum of a first compensation factor computed for siderail 36*a* and a second compensation factor computed for siderail 36*b*. Had any of the other siderails 36 beyond siderails 36*a* and 36*b* changed positioned between FIGS. 7 and 7A, controller 58 would have computed additional compensation factors for those changed siderails and added them to vector 114.

The magnitude and direction of the compensation vectors that are computed for each individual siderail can be determined either empirically or mathematically. When determined empirically, readings from force sensors 60 are taken when an individual siderail 36 is up and when it is down. The difference in the centers of gravity of the load detected by exit detection system between these two positions corresponds to the compensation vector for that individual siderail. Similar readings are taken for the other three siderails and stored in a memory accessible to controller 58. This empirical data is gathered without an occupant on support deck 30 because the change in the center of gravity due to changing positions of the siderails—unlike the changes due to pivot angle 70 changing—are substantially unaffected, or not affected at all, by different occupant weights.

When the compensation vectors are determined mathematically, controller 58 calculates them as a function of the following known parameters: (1) the weight of each siderail 36; and (2) the position of each siderail 36 in coordinate system 86 when in the up position, and the position of each siderail 36 in coordinate system 86 when in the down position. From this data, controller 58 determines how much the center of gravity shifts for each siderail when changing its position and compensates for this change in the center of gravity whenever one or more siderails change their position, as detected by siderails sensors 66*b*.

The amount by which the center of gravity of the load detected by exit detection system 56 is shifted due to a change in the position of a siderail will typically vary depending on additional factors. These additional factors include: (1) pivot angle 70 (at least for the head end siderails 36), (2) tilt angle 72, (3) turn angle 74, (4) and the longitudinal position of support deck 30 relative to litter frame 28. In order to account for these factors, exit detection system 56, in at least one embodiment, gathers empirical data regarding the change in center of gravity for each siderail in each of its different positions as each one of these factors is changed. This empirical data is then processed, stored, and made available to controller 58 so that it can select the appropriate compensation factor for each siderail based on current readings of each of these factors. In an alternative embodiment, the effect on the center of gravity due to these additional factors is computed mathematically by controller 58 using the known parameters discussed above. In still other embodiments, one or more of these additional factors is ignored, or its effect on the center of gravity is approximated, due to its relative insignificance on the center of gravity of the load.

The compensation factor computed by controller 58 for changing positions of the siderails 36 is added to the compensation factor computed by controller 58 for changes in pivot angle 70 (and any of the other compensation factors discussed herein). Thus, if pivot angle 70 changes from, say zero to 45 degrees, controller 58 will apply the appropriate compensation factor for this angular change and the corresponding weight, or weight class, of occupant 82. If, after changing pivot angle to 45 degrees, a user lowers one of the head end siderails, controller 58 will then apply the compensation factor for the lowered siderail at a pivot angle of 45 degrees. If pivot angle 70 changes from 0 degrees to 45 degrees substantially simultaneously with the lowering of one of the head end siderails, controller 58 will apply both compensation factors at substantially the same time, one for the change in pivot angle 70 and the other for the lowering of the siderail 36. The same is true for the other compensation factors discussed herein-they are added together with whatever other compensation factors are appropriate for the changed values (determined at step 100).

Although FIGS. 7-7B only illustrate siderails 36 that have moved from a lowered position to a raised position and vice versa, it is possible that person support apparatus 20 can be constructed to have siderails that are capable of being moved to an intermediate position. In such cases, controller 58 accounts for movement to these intermediate positions in the same manner discussed above. That is, controller 58 determines appropriate compensation factors for each of the types of siderail movement that are possible, i.e. from lowered to intermediate, and from intermediate to raised, and vice versa. These compensation factors may be determined empirically, or mathematically, or by a combination of the two. Controller 58 receives information about the current position of each siderail 36 (lowered, intermediate, or raised) from siderail sensors 66*b* and applies the corresponding compensation factor when any of these positions change.

FIGS. 8-8B illustrate in greater detail one manner in which a tilt angle compensation factor is computed. As shown in FIG. 8, occupant 82 is lying on support deck 30 in the same position relative to support deck 30 as in FIG. 8A.

The difference between FIGS. 8 and 8A is that, in FIG. 8, litter frame 28 is substantially horizontal while in FIG. 8A litter frame 28 has tilted relative to horizontal by tilt angle 72. This tilting changes the distribution of the load sensed by force sensors 60. As a result, exit detection system 56 will detect a center of gravity 110*e* at location (X₅, Y₅) when litter frame 28 is horizontal (FIG. 8), and will detect a center of gravity 110*f* at location (X₆, Y₆) when litter frame 28 is tilted to tilt angle 72 (FIG. 8A). A vector 116 extends between centers of gravity 110*e* and 110*f* in FIG. 8B and corresponds to the compensation factor that is used by exit detection system 56 when litter frame 28 tilts from horizontal to the tilt angle 72 shown in FIG. 7A.

Different compensation factors, and thus different vectors 116, are used by controller 58 depending upon not only the change in tilt angle 72, but also the weight of the occupant. As with the compensation factors for changes in pivot angle 70, exit detection system 56 takes into account different occupant weights through the use of empirically gathered data from multiple occupants of different weight. More specifically, empirical data is gathered for the particular person support apparatus 20 in which exit detection system 56 is implemented that shows the relationship between changes in the detected center of gravity when litter frame 28 tilts and the occupant does not move relative to support deck 30.

In at least one embodiment, the empirical data is gathered and categorized by weight classes of the multiple occupants, such as the weight classes discussed above (e.g. less than 100 pounds, 100-150 pounds, 150-200 pounds, 200-300 pounds, and 300-500 pounds), although other weight classes can be used and/or different demarcations between the weight classes can be used. The empirically gathered data is averaged, or otherwise combined, for all occupants within each weight class. The result of the data is that, for each given weight class, an estimate is provided of the amount by which the detected center of gravity changes for each change in tilt angle 72. This data may be stored in a memory accessible to controller 58, or it may be further processed to define one or more formulas that enable controller 58 to calculate an estimate of the change in the center of gravity for a given occupant weight and a given tilt change 72. Regardless of whether or not the data is stored or a formula is used, controller 58 determines a compensation factor (e.g. vector 116) based upon the occupant's weight (e.g. which weight class he/she is in) and the amount by which tilt angle 72 has changed.

The amount by which the center of gravity of the load detected by exit detection system 56 is shifted due to a change in the tilt angle 72 will also typically vary depending on additional factors, such as: (1) pivot angle 70, (2) the position of the head end siderails 36, and (3) and the longitudinal position of support deck 30 relative to litter frame 28. In at least one embodiment, person support apparatus 20 is constructed such that head section 42 is always parallel to litter frame 28 whenever tilt angle 72 changes from zero, thereby obviating any need to factor in pivot angle 70 when computing a tilt angle compensation. However, in other embodiments, pivot angle 70 can vary independently of tilt angle 72.

In order to account for one or more of the three factors identified above, exit detection system 56, in at least one embodiment, gathers empirical data regarding the change in center of gravity for each tilt angle 72 when head section 42 is pivoted through different pivot angles 70, when each siderail is moved through its different position, and when the longitudinal position of support deck 30 relative to litter frame 28 is moved through each of its positions. This empirical data is then processed, stored, and made available to controller 58 so that it can select the appropriate compensation factor for each tilt angle 72 based on current readings of each of these factors. In an alternative embodiment, the effect on the center of gravity due to these additional factors is computed or estimated mathematically by controller 58 using known parameters regarding the weight and location of each of the moving components (e.g. head section 42, siderails 36, litter frame 28, etc.) In still other embodiments, one or more of these additional factors is ignored, or its effect on the center of gravity is approximated, due to its relative insignificance on the center of gravity of the load.

The compensation factor computed by controller 58 for changing tilt angles 72 is added to the compensation factor (s) computed by controller 58 for any of the other changes that are detected by exit detection system 56 at step 100 of algorithm 68 (FIG. 5). Thus, if a head end siderail 36 is raised subsequent to the tilting of litter frame 28 to a different tilt angle 72, controller 58 will subsequently apply the appropriate compensation factor for this siderail change. If the head end siderail is raised substantially simultaneously with the tilting of litter frame 28, controller 58 will apply both compensation factors at substantially the same time, one for the change in the siderail and the other for the tilting of litter frame 28.

Figures 9, 9A, 9B:
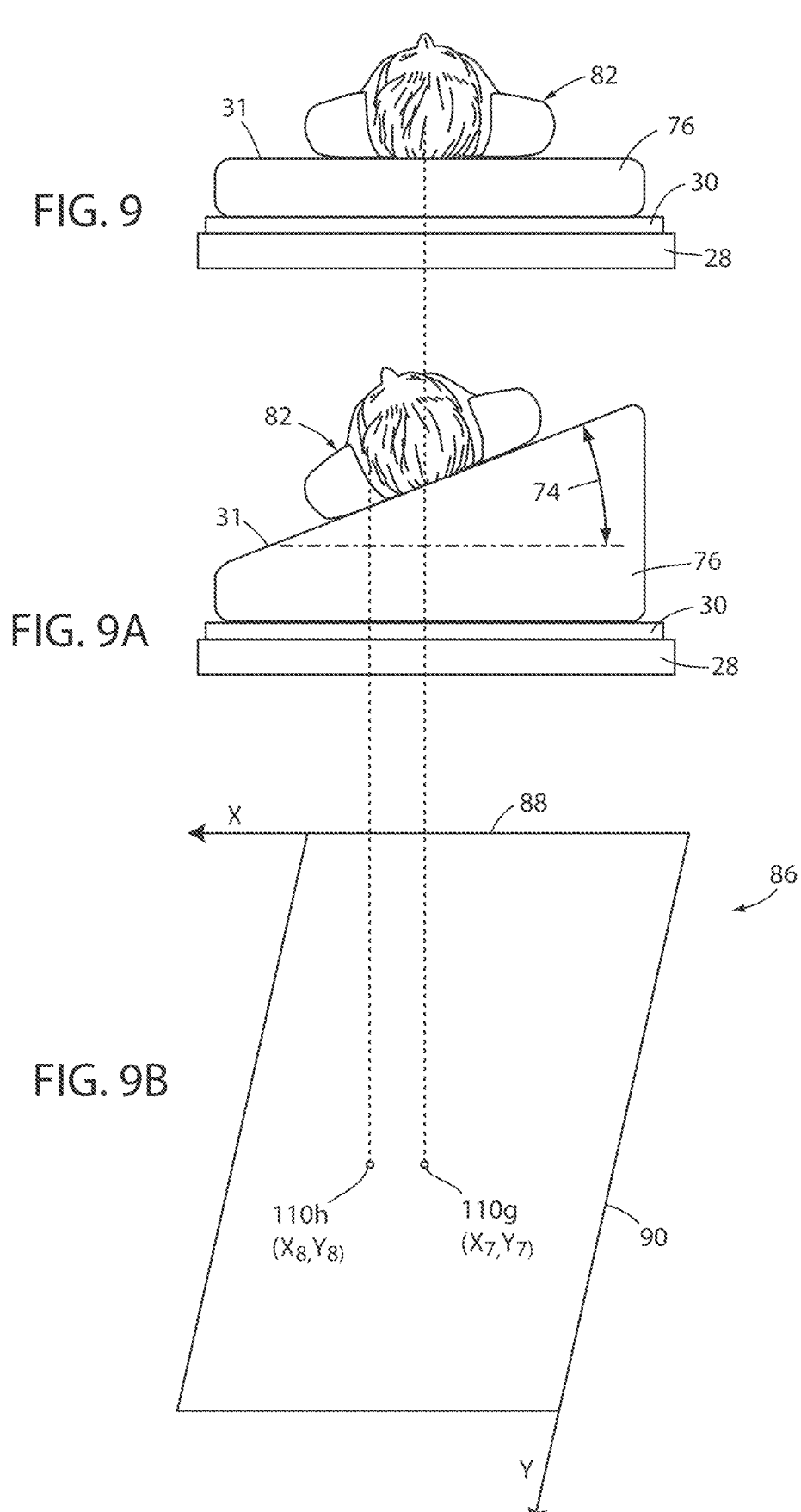
FIG. 9 is an end elevation diagram of a powered mattress, support deck, and litter frame shown with the powered mattress in an flat orientation.
FIG. 9A is an end elevation diagram of the powered mattress, support deck, and litter frame of FIG. 9 shown with one side of the powered mattress inflated to a raised orientation.
FIG. 9B is a perspective view of a planar coordinate system that illustrates changes to the center of gravity caused by the side-to-side turning movement between FIGS. 9 and 9A.

FIGS. 9 and 9A illustrate in greater detail one manner in which a turn angle compensation factor is computed. As shown in FIG. 9, occupant 82 is lying on mattress 76 on top of support deck 30 in the same position relative to mattress 76 as in FIG. 9A. The difference between FIGS. 9 and 9A is that, in FIG. 9, mattress 76 is inflated in such a manner that its top surface is substantially horizontal while in FIG. 9A one or more internal side air bladders within mattress 76 have been inflated to cause the top surface of mattress 76 to be turned to a turn angle 74. The inflation of mattress 76 in the manner shown in FIG. 9A helps turn a patient so as to change the distribution of interface pressures between the top surface of mattress 76 and the skin of the patient, which is helpful in reducing the likelihood of bed sore development.

The turning of occupant 82 via the inflation of one side of mattress 76 changes the distribution of the load sensed by force sensors 60. As a result, exit detection system 56 will detect a center of gravity 110*g* at location (X₇, Y₇) when mattress 76 has its top substantially horizontal (FIG. 9), and will detect a center of gravity 110*h* at location (X₈, Y₈) when mattress 76 has its top surface turned to turn angle 74 (FIG. 9A). A vector 118 extends between centers of gravity 110*g* and 110*h* in FIG. 9B and corresponds to the compensation factor that is used by exit detection system 56 when mattress 76 turns an occupant from the horizontal orientation of FIG. 9 to the turned orientation of FIG. 9A, or vice versa.

Different compensation factors, and thus different vectors 118, are used by controller 58 depending upon not only the change in turn angle 74, but also the weight of the occupant. As with the compensation factors for changes in pivot angle 70 and changes in tilt angle 72, exit detection system 56 takes into account different occupant weights through the use of empirically gathered data from multiple occupants of different weight. More specifically, empirical data is gathered for the particular person support apparatus 20 in which exit detection system 56 is implemented that shows the relationship between changes in the detected center of gravity when mattress 76 is inflated to different turning angles 74 while the occupant does not move relative to support deck 30.

In at least one embodiment, the empirical data is gathered and categorized by weight classes of the multiple occupants, such as the weight classes discussed above (e.g. less than 100 pounds, 100-150 pounds, 150-200 pounds, 200-300 pounds, and 300-500 pounds), although other weight classes can be used and/or different demarcations between the weight classes can be used. The empirically gathered data is averaged, or otherwise combined, for all occupants within each weight class. The result of the data is that, for each given weight class, an estimate is provided of the amount by which the detected center of gravity changes for each turn angle 74. This data may be stored in a memory accessible to controller 58, or it may be further processed to define one or more formulas that enable controller 58 to calculate an estimate of the change in the center of gravity for a given occupant weight and a given turn angle 74. Regardless of whether or not the data is stored or a formula is used, controller 58 determines a compensation factor (e.g. vector 118) based upon the occupant's weight (e.g. which weight class he/she is in) and the amount by which turn angle 74 has changed.

The amount by which the center of gravity of the load detected by exit detection system 56 is shifted due to a change in the turn angle 74 will also typically vary depending on pivot angle 70. However, most person support apparatuses 20 are designed to prevent turning inflation of mattress 76 unless head section 42 is in the substantially horizontal orientation. For those person support apparatuses, exit detection system 56 therefore does not consider pivot angle 70, or any other additional factors when determining the turn angle compensation factor. If person support apparatus 20 is configured to allow mattress 76 to turn an occupant while head section 42 is in a non-horizontal orientation, then controller 58 also utilizes pivot angle 70 when determining the turn angle compensation factor.

In order to account for different pivot angles 70 when determining the turn angle compensation factor, exit detection system 56, in at least one embodiment, gathers empirical data regarding the change in center of gravity for each turn angle 74 when head section 42 is pivoted through different pivot angles 70. This empirical data is then processed, stored, and made available to controller 58 so that it can select the appropriate compensation factor for each turn angle 74 based on current readings of the turn angle 74 and the pivot angle 70.

Exit detection system 56 uses any or all of the aforementioned compensation factors to distinguish between that portion of the change in the center of gravity of the load that is due to patient movement relative to support deck 30 and that portion that is due to movement of one or more components of person support apparatus 20 (e.g. litter frame 28, siderails 36, head section 42, etc.) or that portion that is due to the patient moving in unison with the support surface 31 (e.g. pivoting of head section 42 and/or turning of the occupant via the inflation of a side of mattress 76). The compensation factor accounts for that portion of the movement that is estimated to be due to the latter two factors (component movement or movement in unison with the support surface 31). Any changes in the load's center of gravity beyond those corresponding to the compensation factors are the result of patient movement relative to support surface 31. Those changes are analyzed by controller 58 to determine if the compensated center of gravity has moved out of the currently active zone, which triggers an alert.

In addition to the compensation factors discussed above for pivot angle 70, tilt angle 72, turn angle 74, siderail position, and the longitudinal position of support deck 30, exit detection system 56 also includes, in at least some embodiments, a compensation factor for the height of support deck 30 relative to base 22 and/or a compensation factor for the addition or removal of one or more items—such as, but not limited to, a medical device—onto or from support deck 30.

With respect to changes in the height of support deck 30, it is often the case that lifts 26 cause some shifting of the center of gravity of the sensed load at different heights. In the case where lifts 26 move vertically up and down, it is often the case that lifts 26 will not remain perfectly vertical when extended. Thus, the rectangular shape defined by the vertical axes of each lift and the horizontal axes of base 22 and litter frame 28 will often shift to a more trapezoidal shape when litter frame 28 is raised. This can result in changes to the center of gravity of the load detected by exit detection system 56 that are not related to movement of the occupant relative to support surface 31. In the case where person support apparatus 20 has lifts 26 that include one or more legs whose angular relationship to litter frame 28 changes when the height of litter frame 28 is changed, this too can cause changes in the distribution of weight sensed by force sensors 60. Regardless of the physical construction of lifts 26, exit detection system 56 accounts for these height-dependent changes in the center of gravity in the same manner as has been discussed above with respect to pivot angle 70, tilt angle 72, turn angle 74, and/or changes in the siderail position. That is, controller 58 utilizes readings from height sensor 66e to calculate a compensation factor that is based on empirical data previously gathered, one or more mathematical formulas, or a combination of the two.

With respect to changes in the center of gravity due to the addition or subtraction of an object from litter frame 28, controller 58 determines the position of the added or removed object in coordinate frame of reference 86, as well as the weight of the added or removed object, and mathematically calculates a compensation factor that accounts for this added or removed weight. The detection of an added or removed object, as well as the location of its addition or removal, can be accomplished in multiple different manners. In one manner, the addition or removal of an object is detected in the manner disclosed in commonly assigned U.S. patent application Ser. No. 62/065,242 filed Oct. 17, 2014 by inventors Marko N. Kostic et al. and entitled PERSON SUPPORT APPARATUS WITH MOTION MONITORING, the complete disclosure of which is incorporated herein by reference. The detection of an added or removed object may alternatively or additionally be determined by an image detection system such as that disclosed in commonly assigned U.S. patent application Ser. No. 13/242,022 filed Sep. 23, 2011 by inventors Richard Derenne et al. and entitled VIDEO MONITORING SYSTEM, the complete disclosure of which is also incorporated herein by reference. The detection and/or removal of an object can still further be determined by one or more thermal image sensors, such as those disclosed in commonly assigned U.S. patent application Ser. No. 61/989,243 filed May 6, 2014 by inventors Marko N. Kostic et al. and entitled PERSON SUPPORT APPARATUS WITH POSITION MONITORING, the complete disclosure of which is also incorporated herein by reference. Exit detection system 56 can therefore utilize and/or combine algorithm 68, or any of its modifications, with any of the features and/or algorithms of the systems disclosed in the aforementioned 62/065,242; Ser. No. 13/232,022; and/or 61/989,243 patent applications.

It will be understood by those skilled in the art that the tilt angle compensation factor discussed above and disclosed herein is separate and independent from the known correction factor that is applied when force sensors 60 are implemented as load cells that are only capable of detecting vertical forces applied against them. Correction of such load cell readings is accomplished by multiplying the outputs of the load cells by a known trigonometric factor, as described in more detail in column 17, line 25 through column 21, line 30 of commonly assigned U.S. Pat. No. 7,702,481 entitled DIAGNOSTIC AND CONTROL SYSTEM FOR A PATIENT SUPPORT, the complete disclosure of which is also hereby incorporated herein by reference.

It will also be recognized by those skilled in the art that in any of the embodiments described herein, a shift in the center of gravity of the load detected by force sensors 60 that is due to changes in pivot angle 70 and/or tilt angle 72 is also influenced by how high the occupant 82, mattress 76, and/or other items on support deck 30 extend vertically above litter frame 28. Although variations in this height may influence the center of gravity by an insignificant amount, and thus are ignored in at least one embodiment, at least one other embodiment accounts for this height variation by including data regarding this height. More specifically, in at least one embodiment, exit detection system 56 is in communication with mattress 76. Mattress 76 forwards information to exit detection system 56 regarding any one or more of the following: a type of mattress supported on the support deck (including information indicative of the height of the mattress), an inflation pressure of the mattress, and/or a penetration depth of the occupant into the mattress. Controller 58 is programmed, in at least one embodiment, to use this height information when determining compensation factors for pivot angle 70 and/or tilt angle 72.

As was noted previously, exit detection system 56 can be modified from the embodiment shown in FIG. 4 and described herein to include a different number of sensors 66 and/or to compute a different number of compensation factors. Thus, in one example, exit detection system 56 is modified to include only a pivot angle sensor 66a and to calculate only a compensation factor for pivot angle 70. Such a modified version of exit detection system 56 ignores changes in the center of gravity for siderail positions, tilt angle 72, and turn angle 74. Other combinations of compensation factors and sensors 66 are also possible.

Figure 10:
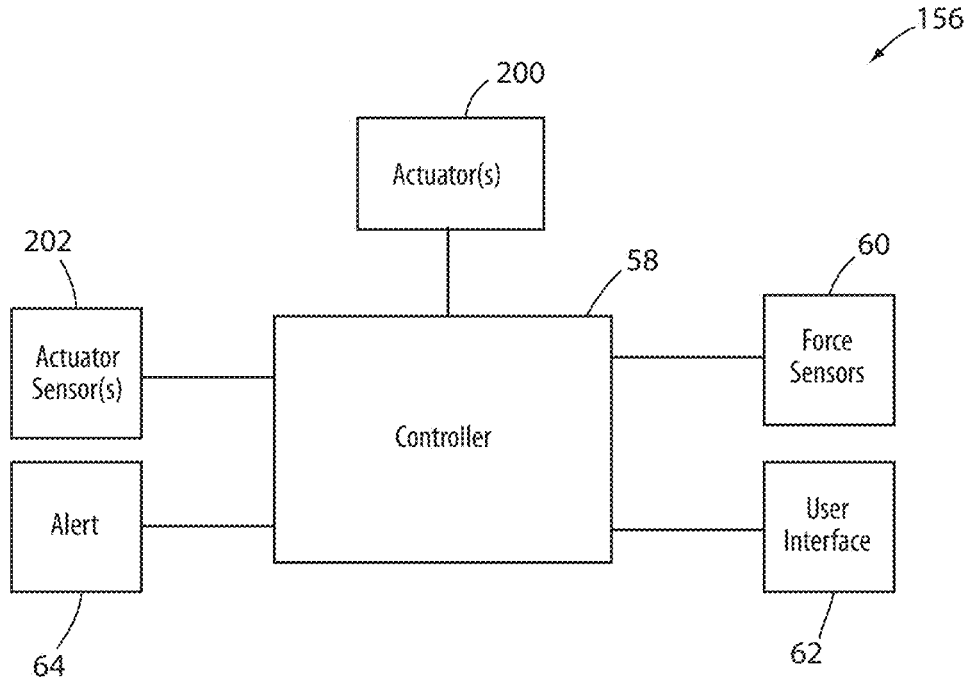
FIG. 10 is a diagram of an exit detection system according to another embodiment of the disclosure.

FIG. 10 illustrates one example of a modified exit detection system 156 that includes several components in common with exit detection system 56. Those components that are the same as those found in exit detection system 56 are labeled with the same reference number and operate in the same manner as previously described, except where otherwise noted. Those components that are different are provided with a new reference number.

Exit detection system 156 includes controller 58, force sensors 60, alert 64, and user interface 62. Exit detection system 156 also includes one or more actuators 200 and one or more actuator sensors 202. Actuators 200 are controlled by controller 58 and carry out any one or more of the movements described previously (e.g. the pivoting of head section 42, the tilting of litter frame 28, the turning movement of mattress 76, the longitudinal movement of support deck 30 relative to litter frame 28, and/or the movement of siderails 36 between their different positions). Actuator sensors 202 sense the position of the various components moved by actuators 200. Actuator sensors 202 therefore may be the same as sensors 66 described previously, depending upon the specific components that are moved by actuators 200 in a particular person support apparatus 20.

Exit detection system 156 operates generally in the same manner as exit detection system 56 previously described. That is, controller 58 determines compensation factors for the movement of the one or more components controlled by actuators 200 and applies these compensation factors to the measured center of gravity. Exit detection system 156 differs from exit detection system 56 in that it includes an automatic calibration feature controlled by one or more controls on user interface 62. When a user activates the automatic calibration feature, controller 58 moves each of components of person support apparatus that are powered by actuators 200 independently while recording the center of gravity changes that result from the movement of these components. Controller 58 analyzes this data to determine updated compensation factors for each of the moved components. The updated compensation factors are then applied to subsequent readings of the center of gravity taken when support deck 30 is occupied by an occupant. The readings taken during the automatic calibration procedure of exit detection system 156 are taken without an occupant on support deck 30, in at least one embodiment. In another embodiment, one or more known weights are used during the automatic calibration process.

It will also be understood by those skilled in the art that the aforementioned compensation factors can be applied to exit detection system that do not determine centers of gravity of the load sensed by the force sensors 60. For example, some conventional exit detection systems monitor the outputs of force sensors, such as load cells, and determine whether an occupant exit alert is to be issued based upon absolute changes in the outputs from individual force sensor readings. Other exit detection systems examine ratios of the sum of forces detected by groups of load cell readings and compare them to sums detected by other load cells. If the ratios change by more than a threshold, an exit alert is issued. Compensation factors such as those discussed herein can be applied to either type of exit detection system, or to still other types of exit detection systems, in order to reduce premature alerts caused by movement of the person support apparatus, and/or to enable changes in the physical configuration of the person support apparatus to be made without having to reset the exit detection system.

Indeed, in at least some embodiments, exit detection system 56 is modified to apply compensation factors directly to the outputs of the force sensors 62, or to some other parameter that is calculated based off of the force outputs other than a center of gravity. In such instances, the exit detection system uses outputs from any one or more of the sensors 66 discussed above to estimate what portion of the change(s) in the force sensors (or other non-center of gravity parameter) are due to the occupant moving relative to support surface 31, and what portion of the change(s) are due to other factors, such as the movement of one or more components of the person support apparatus. The compensation factors are carried out in the same manner as discussed previously. To the extent the compensation factors rely upon empirically gathered data, such empirically gathered data can be gathered from changes in individual force sensor readings (or changes in the non-center of gravity parameters) as the various components of the person support apparatus (e.g. litter frame 28, head section 42, siderails 36, etc.) are moved to their different positions and/or orientations while occupants of different weight classes are positioned on support surface 31 who do not change their position relative to support surface 31 during the gathering of such data.

It will also be understood by those skilled in the art that the principles of the present disclosure can be applied to the exit detection system disclosed in commonly assigned U.S. patent application Ser. No. 62/065,242 filed Oct. 17, 2014 by inventors Marko N. Kostic et al. and entitled PERSON SUPPORT APPARATUS WITH MOTION MONITORING, the complete disclosure of which has already been incorporated herein by reference. In some of the embodiments of the system disclosed in the '242 application, the exit detection system determines a velocity (and/or kinetic energy) of the occupant based upon changes in the occupant's position and issues an exit alert if the velocity exceeds a threshold. The principles disclosed herein can be applied to filter out of the velocity and/or kinetic energy calculations movement that is due components of the person support apparatus 20 moving, rather than movement of the occupant relative to the support surface 31.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A person support apparatus comprising:
   a support deck adapted to support thereon an occupant of the person support apparatus;
   a plurality of force sensors adapted to support the support deck and to detect a load, the load including the support deck and the occupant when the occupant is supported on the support deck;
   a litter frame adapted to support the support deck, the support deck adapted to move forward toward a head end of the litter frame and move rearward toward a foot end of the litter frame;
   a position sensor adapted to determine a position of the support deck on the litter frame; and
   a controller adapted to issue an alert if outputs from the plurality of force sensors meet at least one criterion, the controller taking into account a current position of the support deck on the litter frame when determining whether to issue the alert or not.

2. The person support apparatus of claim 1 wherein the controller is adapted to detect a change in a center of gravity of the load and estimate, using the position of the support deck on the litter frame, what portion of the change is due to movement of the occupant relative to the support deck and what portion of the change is due to a change in the position of the support deck on the litter frame.

3. The person support apparatus of claim 2 wherein the controller is adapted to take into account, when estimating what portion of the change is due to the change in the position of the support deck on the litter frame, a weight of the occupant.

4. The person support apparatus of claim 3 wherein the controller is further adapted to take into account, when estimating what portion of the change is due to the change in the position of the support deck on the litter frame, empirical data indicating a relationship between positions of the support deck on the litter frame and changes in the center of gravity of the load.

5. The person support apparatus of claim 2 further comprising:
   a litter frame angle sensor adapted to determine an angle of the litter frame with respect to horizontal; and
   wherein the controller is further adapted to detect a change in the center of gravity of the load and estimate, using the litter frame angle, what portion of the change is due to movement of the occupant relative to the support deck and what portion of the change is due to tilting of the litter frame.

6. The person support apparatus of claim 5 wherein the controller is further adapted to take into account, when estimating what portion of the change is due to the tilting of the litter frame, a weight of the occupant.

7. The person support apparatus of claim 6 wherein the controller is further adapted to select an occupant weight class based upon the occupant's weight, and to use stored empirical data corresponding to the selected weight class when estimating what portion of the change is due to tilting of the litter frame.

8. The person support apparatus of claim 5 wherein the controller is further adapted to take into account, when estimating what portion of the change is due to the tilting of the litter frame, at least one of the following parameters: a type of mattress supported on the support deck, an inflation pressure of the mattress, or a penetration depth of the occupant into the mattress.

9. The person support apparatus of claim 1 wherein the at least one criterion is a change in the output of at least one of the plurality of force sensors exceeding a threshold.

10. The person support apparatus of claim 1 wherein the plurality of force sensors are a plurality of load cells adapted to support the litter frame.

11. The person support apparatus of claim 3 further comprising:
   a first lift adapted to change a height of a first end of the support deck;
   a second lift adapted to change a height of a second end of the support deck;
   a height sensor adapted to determine a height of the support deck; and
   wherein the controller is further adapted to detect a change in the center of gravity of the load and estimate, using the height of the support deck, what portion of the change is due to movement of the occupant relative to the support deck and what portion of the change is due to a change in height of the support deck.

12. The person support apparatus of claim 11 wherein the controller takes into account, when estimating what portion of the change is due to the change in the height of the support deck, empirical data indicating a relationship between heights of the support deck and changes in the center of gravity of the load.

13. The person support apparatus of claim 2 wherein the plurality of force sensors are a plurality of load cells adapted to support the litter frame.

* * * * *